(12) United States Patent
Scanlan et al.

(10) Patent No.: US 7,645,885 B2
(45) Date of Patent: Jan. 12, 2010

(54) NON-STEROIDAL ANTIANDROGENS

(75) Inventors: Thomas S. Scanlan, Portland, OR (US); Dmitry V. Kadnikov, Dekalb, IL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/467,908

(22) Filed: Aug. 28, 2006

(65) Prior Publication Data

US 2007/0049629 A1 Mar. 1, 2007

Related U.S. Application Data

(60) Provisional application No. 60/711,749, filed on Aug. 26, 2005.

(51) Int. Cl.
C07D 261/20 (2006.01)
C07D 231/54 (2006.01)
A61K 31/416 (2006.01)
A61K 31/42 (2006.01)

(52) U.S. Cl. .................... 548/359.1; 548/241; 514/379; 514/406

(58) Field of Classification Search ............... 548/359.1
See application file for complete search history.

(56) References Cited

U.S. PATENT DOCUMENTS

| | | | |
|---|---|---|---|
| 5,677,336 A | 10/1997 | Jones et al. |
| 5,688,808 A | 11/1997 | Jones et al. |
| 5,688,810 A | 11/1997 | Jones et al. |
| 5,693,646 A | 12/1997 | Jones et al. |
| 5,693,647 A | 12/1997 | Jones et al. |
| 5,696,127 A | 12/1997 | Jones et al. |
| 5,696,130 A | 12/1997 | Jones et al. |
| 5,696,133 A | 12/1997 | Jones et al. |
| 5,994,544 A | 11/1999 | Jones et al. |
| 6,017,924 A | 1/2000 | Edwards et al. |
| 6,093,821 A | 7/2000 | Jones et al. |
| 6,121,450 A | 9/2000 | Jones et al. |
| 6,448,405 B1 | 9/2002 | Jones et al. |
| 6,451,834 B1 | 9/2002 | Arnold et al. |
| 6,462,036 B1 | 10/2002 | Doyle et al. |
| 6,518,294 B2 | 2/2003 | Teng et al. |
| 6,534,516 B1 | 3/2003 | Edwards et al. |
| 6,566,372 B1 | 5/2003 | West et al. |
| 6,667,313 B1 | 12/2003 | Hamann et al. |
| 6,696,459 B1 | 2/2004 | Jones et al. |
| 6,831,093 B2 | 12/2004 | Scanlan et al. |
| 7,026,484 B2 | 4/2006 | Zhi et al. |
| 7,071,333 B2 | 7/2006 | Combs et al. |
| 7,109,196 B2 | 9/2006 | Wang et al. |
| 7,122,570 B2 | 10/2006 | Koppitz et al. |
| 7,132,533 B2 | 11/2006 | Benedict et al. |
| 2002/0183314 A1 | 12/2002 | Higuchi et al. |
| 2002/0183346 A1 | 12/2002 | Zhi et al. |
| 2003/0130505 A1 | 7/2003 | Zhi et al. |
| 2003/0186970 A1 | 10/2003 | Higuchi et al. |
| 2005/0054700 A1 | 3/2005 | Scanlan et al. |

FOREIGN PATENT DOCUMENTS

| | | |
|---|---|---|
| WO | WO99/33786 | 7/1999 |
| WO | WO99/41257 | 8/1999 |
| WO | WO03/086294 | 10/2003 |
| WO | WO2004/026248 | 4/2004 |
| WO | WO2004/075840 | 9/2004 |
| WO | WO 2004/075840 A2 * | 9/2004 |
| WO | WO2004/093805 | 11/2004 |
| WO | WO2005/018573 | 3/2005 |

OTHER PUBLICATIONS

Medical Encyclopedia: Prostate Cancer [online], [retrieved on Sep. 24, 2007]. Retrieved from the Internet, URL; http://www.nlm.nih.gov/medlineplus/ency/article/000380.htm>.*
Medical Encyclopedia: Androgen insensitivity syndrome [online], [retrieved on Sep. 24, 2007]. Retrieved from the Internet, URL; http://www.nlm.nih.gov/medlineplus/ency/article/001180.htm>.*
NINDS Kennedy's Disease Information Page [online], [retrieved on Sep. 24, 2007]. Retrieved from the Internet, URL; http://www.ninds.nih.gov/disorders/kennedys/kennedys.htm>.*
Facts about SMA [online], [retrieved on Sep. 24, 2007]. Retrieved from the Internet, URL; http://www.mdausa.org/publications/fa-sma-qa.html>.*
Vippagunta,et al. Advanced Drug Delivery Reviews 48 (2001) 3-26.*
Prostate cancer [online], retrieved on May 6, 2009, retrieved from the internet {URL; http://www.healthline.com/adamcontent/prostate-cancer}.*
International Search Report for PCT/US2006/033732, dated Jul. 24, 2007.
Amjad Ali, et al., "Novel N-Arylpyrazolo[3,2-c] Based Ligands for the Glucocorticoid Receptor: Receptor Binding and in Vivo Activity," *J. Med. Chem.* 47:2441-2452 (2004).
Miguel Beato, "Gene Regulation by Steroid Hormones," *Cell* 56:335-344 (1989).
Cameron J. Smith, "Novel ketal ligands for the glucocorticoid receptor: in vitro and in vivo activity," *Bioorganic & Medicinal Chemistry Letters*, 15:2926-2931(2005).
Christopher F. Thompson, et al, "Novel Heterocyclic Glucocorticoids: In Vitro Profile and In Vivo Efficacy," *Bioorganic & Medicinal Chemistry Letters* 15:2163-2167 (2005).
Balog, A., et al., "The Synthesis and Evaluation of [2.2.1 [-bicycloazahydantoins as Androgen Receptor Antagonists," *Bioorganic and Medicinal Chemistry Letters*, 14:6107-6711(2004).
Barrack, E.R., et al., "Androgen Receptor Gene Mutations in Human Prostate Cancer," *J. Cell. Biochem.*, 16D:93 (1992).
Blauer, M., et al., "Location of Androgen Receptor in Human Skin," *J. Investigat. Derm.*, 97:264-268 (1991).

(Continued)

*Primary Examiner*—Rei-Tsang Shiao
*Assistant Examiner*—Shawquia Young
(74) *Attorney, Agent, or Firm*—Fish & Richardson P.C.

(57) ABSTRACT

The invention provides non-steroidal ligands for the androgen receptor, methods for making non-steroidal ligands of the androgen receptor, compositions of non-steroidal ligands of the androgen receptor and methods of using non-steroidal ligands and compositions of non-steroidal ligands of the androgen receptor for treating or preventing diseases (e.g., prostate cancer) associated with androgen binding to the androgen receptor.

22 Claims, 11 Drawing Sheets

OTHER PUBLICATIONS

Coghlan, M. J., Elmore, S. W., et al., Chapter 17: Selective Glucocorticoid Recptor Modulators, Annual Reports in Medicinal Chemistry, vol. 37, (2002).

Demura, T., et al., "Establishment of Monoclonal Antibody to Human Androgen Receptor and Its Clinical Application for Prostatic Cancer," *Am. J. Clinical Oncol.* 11 (Suppl. 2), S23-S26 (1988).

Gottlieb, B., et al., "Variable Expressivity and Mutation Databases: The Androgen Receptor Gene Mutations Database," *Human Mutation*, 17:382-388 (2001).

Gottlieb, B., et al., "Androgen Insensitivity," *American J. Medical Genetics* (Semin. Med. Genet.), 89:210-217 (1999).

Hamann, L. G. et al., "Synthesis and Biological Activity of a Novel Series of Nonsteroidal, Peripherally Selective Androgen Receptor Antagonists Derived from1,2-Dihydropyridono[5,6-g]quinolines," *Journal of Medicinal Chemistry*, 41(4), 623-639, (1998).

Hamann, L.G., et al., "Discovery of a Potent, Orally Active, Nonsteroidal Androgen Receptor Agonist: 4-Ethyl-1,2,3,4-tetrahydro-6- (trifluoromethyl)-8-pyridono [5,6-g]-quinoline (LG121071)", *Journal of Medicinal Chemistry*, 42(2): 210-212 (1999).

Ishioka, T., et al., "Novel Non-Steroidal/Non-Aniline Type Androgen Antagonists with an Isoxazolone Moiety," *Bioorganic and Medicinal Chemistry*, 10(5): 1555-1566 (2002).

Ishioka, T., et al., "Anti-Androgens with full antagonistic activity toward human prostate tumor LNCaP cells with mutated androgen receptor" *Bioorganic and Medicinal Chemistry Letters*, 13(16): 2655-2658 (2003).

Keller, et al., Frontiers in Bioscience, 1:59-71 (1996).

Kong, J. W., et al., "Effects of isosteric pyridone replacements in androgen receptor antagonists based on 1,2-dihydro- and 1,2,3,4-tetrahydro-2,2-dimethy1-6-trifluoromethyl-8-pyridono[5,6-g]quinolines," *Bioorganic and Medicinal Chemistry Letters*, 10:411-414 (2000).

McLeod, D.G., "Antiandrogenic Drugs," *Cancer*, 71(3):1046-1049 (1993).

Miyachi, H., et al., "Potent novel nonsteroidal androgen antagonists with a phthalimide skeleton", *Bioorganic and Medicinal Chemistry Letters*, 7(11): 1483-1488 (1997).

Nelson, et al., "Androgen Receptor CAG Repeats and Prostate Cancer," *Am. J. Epidemiology*, 155:883-890 (2002).

Salvati, M.E., et al., "Structure Based Approach to the Design of Bicyclic-1H-isoindole-1,3(2Hdione Based Androgen Receptor Antagonists ," *Bioorganic and Medicinal Chemistry Letters*, 15:271-276 (2005).

Salvati, M. E., et al., "Identification of a Novel Class of Androgen Receptor Antagonists Based on the Bicyclic-1H-isoindole-1.3(2H)-dione Based Nucleus," *Bioorganic and Medicinal Chemistry Letters*, 15:389-393 (2005).

See, W. A., et al., "Bicalutamide as Immediate Therapy Either Alone or as Adjuvant to Standard Care of Patients with Localized or Locally Advanced Prostate Cancer:First Analysis of the Early Prostate Cancer Program," *The Journal of Urology*, 168:429-435 (2002).

Taplin, M.E., et al., "Mutation of the Androgen-Receptor Gene in Metastatic Androgen-independent Prostate Cancer," *New Eng. J. Med.*, 332:1393-1398 (1995).

Tenbaum, S., et al., "Nuclear Hormone Receptors: Structure, Function and Involvement in Disease," *Int. J. Biochem. And Cell Biol.*, 29:1325-1341 (1997).

Tucker, H., et al., "Nonsteroidal antiandrogens: Synthesis and structure-activity relationships of 3-substituted derivatives of 2-hydroxypropionanilides", Journal of Medicinal Chemistry, 31(5): 954-959, (1988).

Yamamoto, K., "Steroid Receptors Regulated Transcription of Specific Genes and Gene Network," *Ann. Rev. Genetics*, 19, 209, (1985).

Zhuang, Y. H., et al., "Subcellular Location of Androgen Receptor in Rat Prostate, Seminal Vesicle and Human Osteosarcoma MG-63," *J. Steroid Biochem. And Molec. Biol.*, 41:693-696 (1992).

Zhi, L., et al., "Switching Androgen Receptor Antagonists to Agonists by Modifying C-Ring Substituents on Piperidino[3,2-g]quinolone," *Bioorganic and Medicinal Chemistry Letters*, 9:1009-1012, (1999).

Zhi, L., and E. Martinborough, "Selective Androgen Receptor Modulators (SARMs)," *Annual Reports in Medicinal Chemistry*, 36:169-180 (2001).

\* cited by examiner

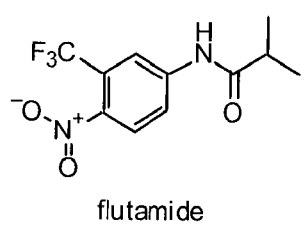
flutamide
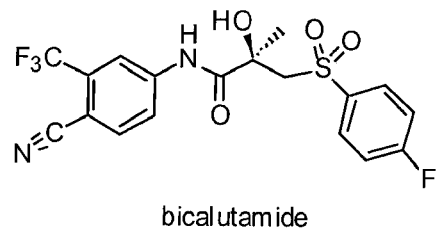
bicalutamide
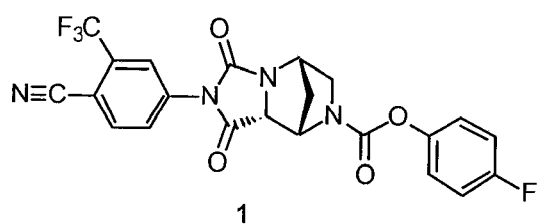
1
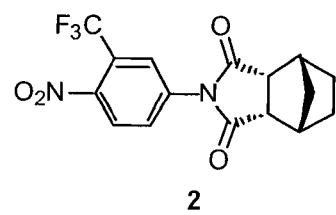
2
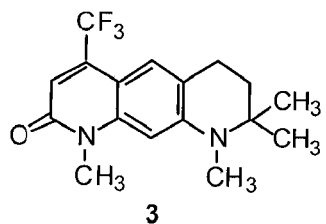
3
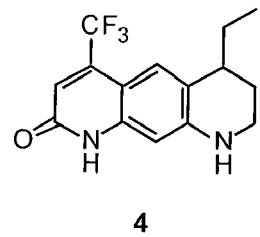
4
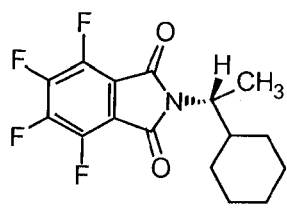
5
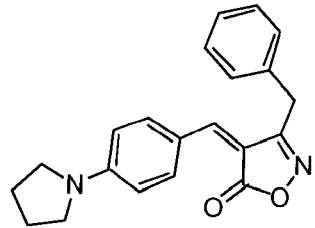
6
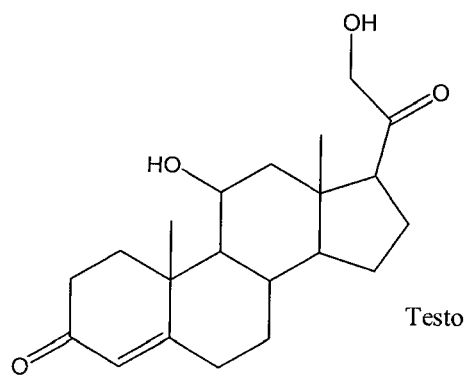
Testosterone
FIG. 1

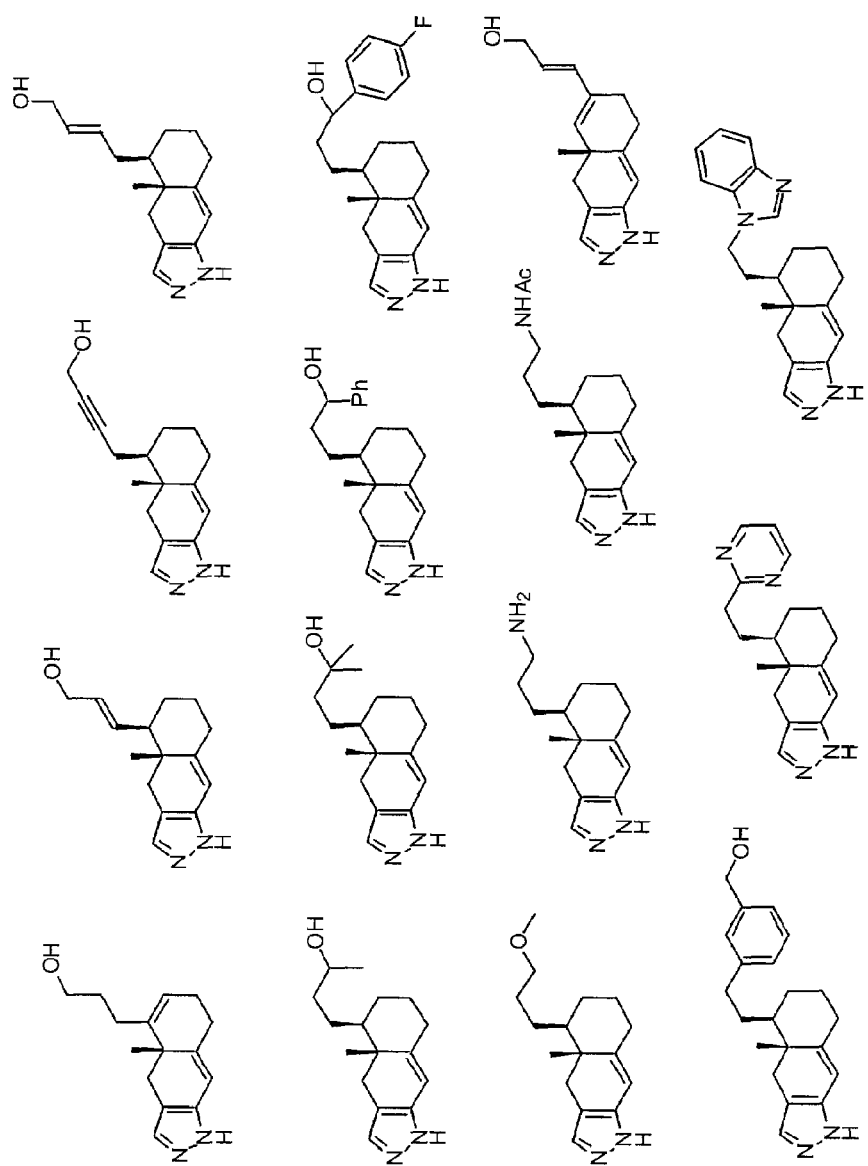
FIG. 6 (page 1 of 2)

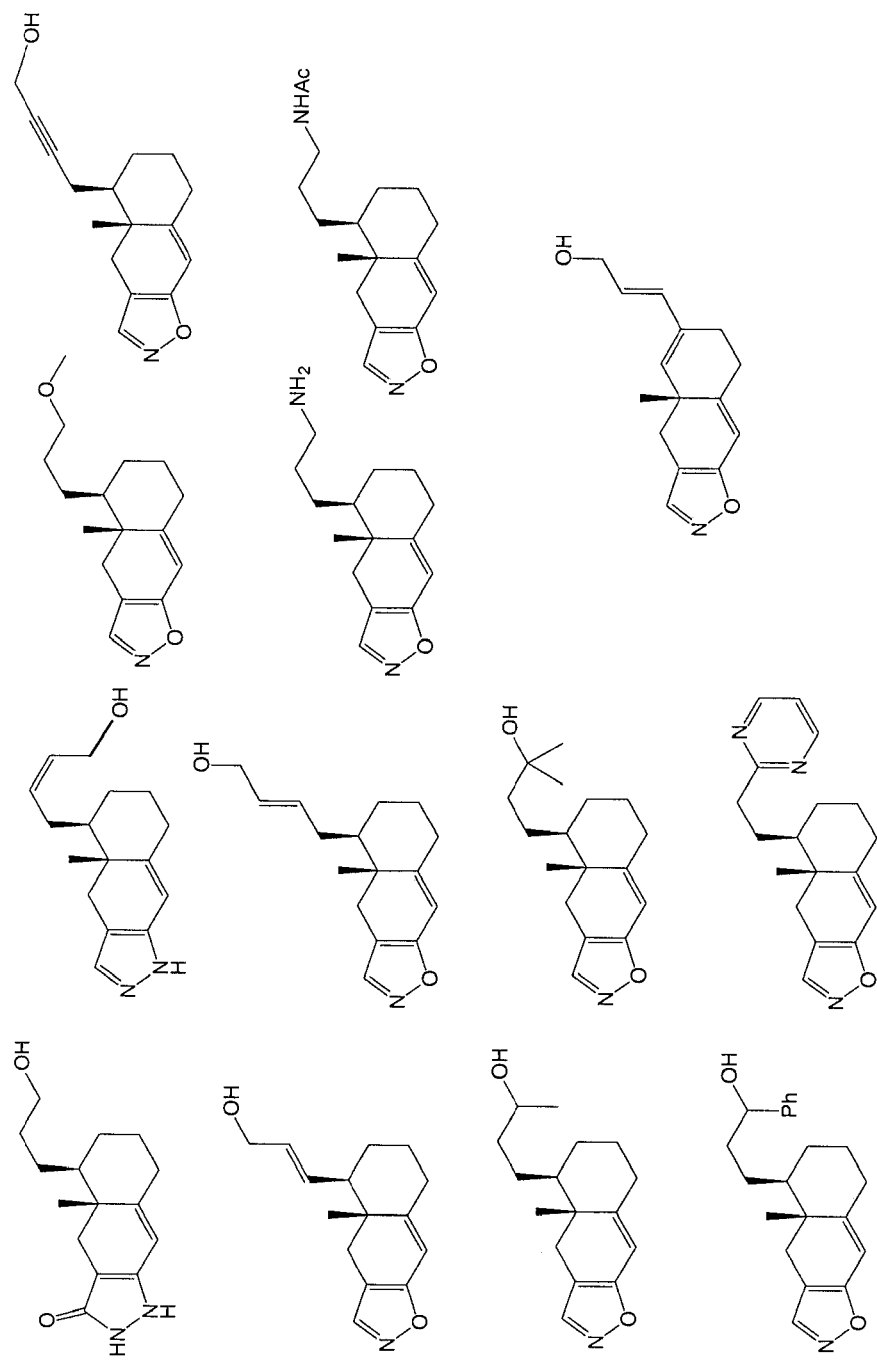
FIG. 6 (page 2 of 2)

NON-STEROIDAL ANTIANDROGENS

CLAIM OF PRIORITY

The present application claims the benefit of priority to U.S. provisional application Ser. No. 60/711,749, filed Aug. 26, 2005, which is incorporated herein by reference in its entirety.

STATEMENT REGARDING FEDERALLY SPONSORED RESEARCH

This invention was made with government support under grant No. CA89502 awarded by the National Institutes of Health. The government has certain rights in the invention.

FIELD OF THE INVENTION

The present invention generally relates to non-steroidal ligands of the androgen receptor. The invention relates more particularly to non-steroidal ligands for the androgen receptor that are based on a carbocyclic ring system, annelated with a heterocyclic ring, methods for making such ligands, compositions comprising such ligands, and methods for using the same.

BACKGROUND

The Androgen Receptor (AR) is an intra-cellular receptor that is a key factor in mediating a wide variety of physiological processes, including regulation of male development, and the behavior of the prostate (see, e.g., Keller, et al., *Frontiers in Bioscience*, 1:5971, (1996)).

AR is a member of the family of nuclear receptor (NR's), nearly all of which are medically significant (see, e.g., Gronemeyer and Laudet, *The Nuclear Receptor Facts Book*, Academic Press, (2002)). Nuclear receptors are a superfamily of proteins that specifically bind a physiologically relevant small molecule, such as a hormone. Generally, the binding occurs with high affinity so that apparent $K_d$'s are commonly in the 0.01-20 nM range, depending on the nuclear receptor/ligand pair. The principal action of NR's is to modulate, i.e., enhance or repress, the transcription of DNA. Unlike integral membrane receptors and membrane associated receptors, the nuclear receptors reside in either the cytoplasm or nucleus of eukaryotic cells. As a result of a molecule, such as a hormone, binding to a nuclear receptor, the nuclear receptor changes the ability of a cell to transcribe DNA. Specifically, the nuclear receptors, and in particular AR, regulate gene expression by interacting with specific DNA sequences of target genes (see, e.g., Yamamoto, K., "Steroid receptors regulated transcription of specific genes and gene network," *Ann. Rev. Genetics*, 19, 209, (1985); and Beato, M., "Gene regulation by steroid hormones", *Cell*, 56:335-344, (1989)).

AR binds hormones, referred to as "androgens", which include male sex steroids, such as testosterone and 5α-dihydrotestosterone (DHT). The major role of these hormones is the development and maintenance of the male reproductive system and secondary sexual characteristics. In particular, testosterone is responsible for initiating and maintaining spermatogenesis, and the virilization of male internal sex organs, while DHT causes development of external sex organs, as well as secondary sexual characteristics. Androgens also have a variety of anabolic effects, such as increase in mineral bone density, muscle size and strength. Their effects on hair, skin, as well as male behavior are also well known. In normal physiological action, AR plays a role in embryogenesis, homeostasis, the development of sexual organs, reproduction, and cell growth and death in many classes of cells. However, in pathological conditions, AR is implicated in prostate cancers, androgen insensitivity syndromes (AIS), and spinal and bulbar muscular atrophy (Kennedy's disease).

In essence, upon androgen hormone binding, AR binds to DNA, and then acts as a transcription factor that regulates the expression of from about 20 to hundreds of genes depending on the cell type (see, e.g., Keller, E. T., et al., *Frontiers in Bioscience*, 1:5971, (1996); and, Beato, M., "Gene regulation by steroid hormones," *Cell*, 56: 335-344, (1989)). However, the underlying mechanism is actually more complicated. It is understood that activation of AR, initiated by binding of a hormone such as DHT to the AR ligand binding domain (LBD), changes the three dimensional structure of the LBD, and causes AR to dissociate from chaperones in the cytoplasm and travel into the nucleus where the receptor binds response elements on DNA. This mechanism is effectively a kind of control that ensures that androgen receptors are kept away from DNA molecules until they have been suitably activated.

Androgens have a variety of effects on different tissues in the body. The androgen receptor has wide tissue distribution as can be demonstrated by immunohistochemistry in several tissues e.g., prostate (Zhuang, Y. H., Blauer, M., Pekki, A., et al., "Subcellular location of androgen receptor in rat prostate, seminal vesicle and human osteosarcoma MG-63", *J. Steroid Biochem. and Molec. Biol.*, 41:693-696, (1992)), skin (see, e.g., Blauer, M., Vaalasti, A., Pauli, S-L., et al., "Location of androgen receptor in human skin", *J. Investigat. Derm.*, 97:264-268, (1991)), and oral mucosa. The presence of the androgen receptor can also be demonstrated in a diverse range of human tumors, e.g., osteosarcoma (Zhuang, et al., *J. Steroid Biochem. and Molec. Biol.*, 41:693-696, (1992)). In prostatic carcinoma, androgen receptor expression may be of clinical relevance (see, e.g., Demura, T., Kuzumaki, N., Oda, A., et al., "Establishment of monoclonal antibody to human androgen receptor and its clinical application for prostatic cancer", *Am. J. Clinical Oncol.*, 11(2):S23-S26, (1988)). Mutation of the gene encoding androgen receptor has been reported in prostatic carcinoma (Barrack, E. R., Newmark, J. R., Hardy, D. O., et al., "Androgen receptor gene mutations in human prostate cancer", *J. Cell Biochem.*, 16D:93, (1992)). Nevertheless, the mechanisms of AR tissue selectivity are only starting to be understood. Development of novel AR ligands that possess tissue specificity would provide new tools for uncovering these mechanisms. Androgen receptor ligands would also have a major therapeutic potential in treating numerous diseases.

Of particular significance, AR has been implicated in the development of prostate cancer and benign prostatic hyperplasia. Prostate cancer is the second leading cause of cancer deaths among men in the United States, and it has a complex etiology (see, e.g., Nelson, K. A., and Witte, J. S., "Androgen Receptor CAG Repeats and Prostate Cancer", *Am. J. Epidemiology*, 155:883-890, (2002)). In particular, unregulated AR activity is implicated in metastatic prostate cancers (see, Tenbaum, S., and Baniahmad, A., "Nuclear Hormone Receptors: Structure, Function and Involvement in Disease," *Int. J. Biochem. and Cell Biol.*, 29:1325-1341, (1997); Taplin, M. E., Shuster, G. J., Frantz, M. E., Spooner, A. E., Ogata, G. K., Keer, H. N., and Balk, S. P., "Mutation of the androgen-receptor gene in metastatic androgen-independent prostate cancer," *New Eng. J. Med.*, 332:1393-1398, (1995); Gottlieb, B., Beitel, L. K., and Trifiro, M., "Variable Expressivity and Mutation Databases: The Androgen Receptor Gene Mutations Database," *Human Mutation*, 17:382-388, (2001))

which are the most common forms of malignancy in men, and androgen insensitivity syndromes (Gottlieb, B., Pinsky, L., Beitel, L. K., and Trifiro, M., "Androgen Insensitivity," *American J. Medical Genetics* (Semin. Med. Genet.), 89, 210-217, (1999)), but its role is not yet fully understood. Consequently, current research in prostate cancer is aimed at finding new ways to inhibit AR function in pathological states.

Currently, non-steroidal AR antagonists are used clinically to treat early stages of prostate cancer (see, e.g., McLeod, D. G., "Antiandrogenic Drugs," *Cancer*, 71(3), 1046-1049, (1993)). However, these agents still cause undesirable side effects, such as breast tenderness and gynecomastia (see, e.g., See, W. A., et al., "Bicalutamide as Immediate Therapy Either Alone or as Adjuvant to Standard Care of Patients with Localized or Locally Advanced Prostate Cancer: First Analysis of the Early Prostate Cancer Program," *The Journal of Urology*, 168, 429-435, (2002)). Moreover, their effect ceases as the prostate cancer progresses to androgen-independent stages.

While there is considerable interest in developing selective AR modulators, the number of ligands developed thus far is still limited. Current treatment of prostate cancer is often with anti-testosterones, such as flutamide (Eulexin, or cyproterone acetate), nilutamide, and bicalutamide (casodex), which suppress AR function. Flutamide and bicalutamide, whose structures are shown in FIG. 1, were the earliest non-steroidal AR antagonists developed and are aniline derivatives containing strong electron-withdrawing substituents such as nitro or cyano (see, e.g., Tucker, H., Crook, J. W., and Chesterson, G. J., "Nonsteroidal antiandrogens: Synthesis and structure-activity relationships of 3-substituted derivatives of 2-hydroxypropionanilides", *Journal of Medicinal Chemistry*, 31(5), 954-959, (1988)). However, after 3-5 years of treatment with these agents, the treatment becomes less effective. In particular, prostate-specific antigen (PSA) levels are seen to rise in patients; the presence of such antigens indicates AR activation. The rise in malignant transcriptional activity has been attributed to AR being activated inappropriately.

Recently, several other scaffolds for non-steroidal AR ligands have been reported. Several sets of ligands that combine structural features of bicalutamide and flutamide with [2.2.1]-bicycloazahydantoins (structure 1 in FIG. 1) (Balog, A., et al., "The synthesis and evaluation of [2.2.1]-bicycloazahydantoins as androgen receptor antagonists," *Bioorganic and Medicinal Chemistry Letters*, 14, 6107-6711, (2004)) or bicyclic 1H-isoindole-1,3(2H)-dione (structure 4 in FIG. 1) (Salvati, M. E., et al., "Identification of a novel class of androgen receptor antagonists based on the bicyclic-1H-isoindole-1,3(2H)-dione nucleus," *Bioorganic and Medicinal Chemistry Letters*, 15, 389-393, (2005); Salvati, M. E., et al., "Structure based approach to the design of bicyclic-1H-isoindole-1,3(2H)-dione based androgen receptor antagonists," *Bioorganic and Medicinal Chemistry Letters*, 15, 271-276, (2005)) scaffolds have been developed.

A number of ligands based on 4-trifluoromethyl-2-quinolone scaffold, for example structures 3 and 4 (Hamann, L. G., et al., "Synthesis and Biological Activity of a Novel Series of Nonsteroidal, Peripherally Selective Androgen Receptor Antagonists Derived from 1,2-Dihydropyridono[5,6-g]quinolines," *Journal of Medicinal Chemistry*, 41(4), 623-639, (1998); Konga, J. W., et al., "Effects of isosteric pyridone replacements in androgen receptor antagonists based on 1,2-dihydro- and 1,2,3,4-tetrahydro-2,2-dimethyl-6-trifluoromethyl-8-pyridono[5,6-g]quinolines," *Bioorganic and Medicinal Chemistry Letters*, 10, 411-414, (2000)) have also been developed. Varying the substitution pattern on the outer ring afforded a series of ligands with a spectrum of effects, from full agonism to full antagonism (Hamann, L. G., et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", *Journal of Medicinal Chemistry*, 42(2), 210-212, (1999); Zhi, L., et al., "Switching Androgen Receptor Antagonists to Agonists by Modifying C-Ring Substituents on Piperidino[3,2-g]quinolone," *Bioorganic and Medicinal Chemistry Letters*, 9, 1009-1012, (1999)).

Substituted phthalimides (structure 5) have also been shown to be efficient AR ligands (Miyachi, H., et al., "Potent novel nonsteroidal androgen antagonists with a phthalimide skeleton", *Bioorganic and Medicinal Chemistry Letters*, 7(11), 1483-1488, (1997)). Recently, ligands based on the iso-oxazolidinone scaffold (structure 6) have been reported to be up to 200 times more potent than flutamide (Ishioka, T., et al., "Novel Non-Steroidal/Non-Aniline Type Androgen Antagonists with an Isoxazolone Moiety," *Bioorganic and Medicinal Chemistry*, 10(5), 1555-1566, (2002); Ishioka, T., et al., "Anti-Androgens with full antagonistic activity toward human prostate tumor LNCaP cells with mutated androgen receptor" *Bioorganic and Medicinal Chemistry Letters*, 13(16), 2655-2658, (2003)). Moreover, unlike flutamide, these ligands act as antagonist even on the mutated AR (for example, in LNCaP cells) (Ishioka, T., et al., *Bioorg. and Med. Chem. Lett.*, 13(16), 2655-2658, (2003)).

The other principal therapeutic application of androgen receptor ligands is to male hormone replacement therapy. The level of testosterone decreases significantly in older men, thus resulting in osteopenia and loss of lean body mass. Nevertheless, the use of endogenous androgens and steroidal AR agonists in male hormone replacement therapy is limited due to a variety of undesirable side effects (see, e.g., Zhi, L., and E. Martinborough, "Selective Androgen Receptor Modulators (SARMs)," *Annual Reports in Medicinal Chemistry*, 36, 169-180, (2001)). Thus, development of a selective AR modulator with androgen effect in bones and muscles, but not in the prostate, would be highly desirable. Tissue-selective AR modulators can also be used for treatment of reproductive disorders and male hypogonadism (see, e.g., Zhi, L., *Ann. Repts. in Med. Chem.*, 36, 169-180, (2001)).

Thus, compounds that exhibit tissue selective antagonism for the androgen receptor remain desirable and have yet to be satisfactorily developed.

The discussion of the background to the invention herein is included to explain the context of the invention. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present invention addresses the need for tissue-selective anti-androgens, and other needs, by providing non-steroidal ligands for the androgen receptor, methods for making non-steroidal ligands of the androgen receptor, compositions of non-steroidal ligands of the androgen receptor, and methods of using non-steroidal ligands of the androgen receptor and compositions thereof for treating or preventing diseases (e.g., prostate cancer, benign prostatic hyperplasia, reproductive disorders, and male hypogonadism) associated with androgen binding to the androgen receptor. In principle, the current invention allows for the preparation of either agonist or antagonist compounds and either or both of these pharmacological modes of action may be useful for certain therapeutic treatments.

The compounds of the instant invention include a carbocyclic ring system, which may be unsaturated and is annelated with a heterocyclic ring. In particular, the carbocyclic ring systems may be an indan (i.e., a six membered carbocyclic ring fused with a five membered carbocyclic ring), a dehydrodecalin (i.e., a six membered carbocyclic ring fused with a six membered carbocyclic ring) or a dehydro [4.5.0] bicyclo undecane (i.e., a six membered carbocyclic ring fused with a seven membered carbocyclic ring) ring system. The heterocyclic ring annelated with the carbocyclic ring system is typically attached to the six membered ring fragment—say of an indan or a dehydro-decalin—and has at least one nitrogen atom, or a nitrogen and an oxygen atom. The compounds of the instant invention have formulae Ia, Ib, IIa, IIb, IIIa, IIIb, IIIc, IVa, IVb, or IVc.

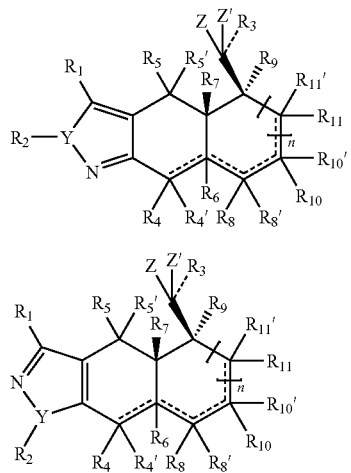

In particular, the compounds of the present invention have structural formulae Ia or Ib, or a pharmaceutically available salt, solvate, or hydrate thereof wherein:

Y is nitrogen or oxygen, and when Y is oxygen, $R_2$ is absent;

Z is hydrogen, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, chloro, bromo, iodo, thio, heteroaryl, substituted heteroaryl, heteroalkyl, substituted heteroalkyl, heteroarylalkyl, substituted heteroarylalkyl, or is absent;

Z' is hydrogen, or is absent;

n is 0, 1, or 2;

$R_1$ is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroaryl, substituted heteroaryl, heteroalkyl, substituted heteroalkyl, heteroarylalkyl, or substituted heteroarylalkyl;

$R_2$ is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m W$, —$CR=CR'W$, $=CRW$, or $C≡CW$, wherein m=1-10;

R and R' is each independently hydrogen, cyano, nitro, halo, thio, carboxy, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, or thio;

the bond in formulae Ia and Ib that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae Ia and Ib that are shown with single and dashed lines is a double bond and one or more of $R_4'$, $R_8'$, $R_{10}'$, and $R_{11}'$ is absent, such that normal valences of carbon atoms in the rings are satisfied.

Furthermore, the compounds of the present invention are according to formulae IIa or IIb,

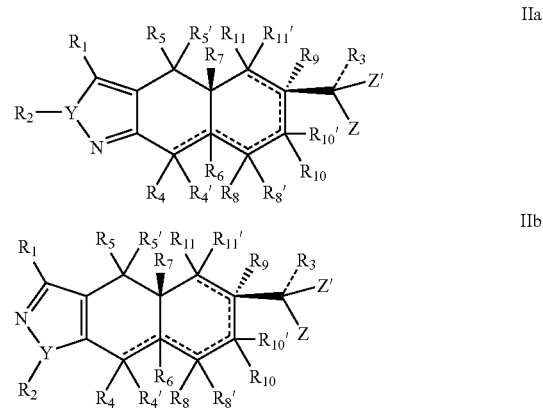

or a pharmaceutically available salt, solvate, or hydrate thereof wherein:

Y is nitrogen or oxygen, and when Y is oxygen, $R_2$ is absent;

Z is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, fluoro, chloro, bromo, iodo, thio, hydroxyl, thio, heteroaryl, substituted heteroaryl, heteroalkyl, substituted heteroalkyl, heteroarylalkyl, substituted heteroarylalkyl, or is absent;

Z' is hydrogen, or is absent;

$R_1$ is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroaryl, substituted heteroaryl, heteroalkyl, substituted heteroalkyl, heteroarylalkyl, or substituted heteroarylalkyl;

$R_2$ is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m W$, —$CR\!=\!CR'W$, $=\!CRW$, or $C\!\equiv\!CW$, wherein m=0-10;

R and R' is each independently hydrogen, cyano, nitro, halo, thio, carboxy, hydroxyl, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, substituted alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, hydroxyl, thio, or is absent;

the bond in formulae IIa and IIb that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IIa and IIb that are shown with single and dashed lines is a double bond and one or more of $R_4'$, $R_8'$, $R_9$, $R_{10}'$, and $R_{11}'$ is absent, such that normal valences of carbon atoms in the rings are satisfied.

The present invention still further includes compounds according to structural formulae IIIa, IIIb or IIIc, or a pharmaceutically available salt, solvate, or hydrate thereof wherein:

Y is nitrogen, and in structures IIIa and IIIb, Y can also be oxygen;

Z is hydrogen, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, chloro, bromo, iodo, thio, heteroaryl, substituted heteroaryl, heteroalkyl, substituted heteroalkyl, heteroarylalkyl, substituted heteroarylalkyl, or is absent;

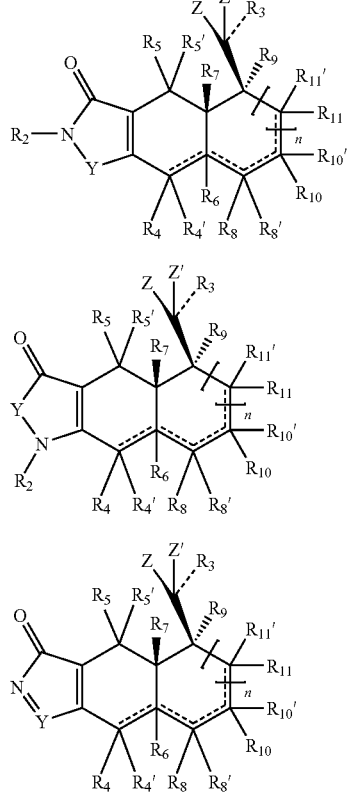

Z' is hydrogen, or is absent;

n is 0, 1, or 2;

$R_2$ is present in IIIa and IIIb, but not IIIc, and is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is $-(CRR')_m W$, $-CR=CR'W$, $=CRW$, or $C\equiv CW$, wherein m=1-10;

R and R' is each independently hydrogen, cyano, nitro, halo, thio, carboxy, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, or thio;

the bond in formulae IIIa, IIIb and IIIc that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IIIa, IIIb and IIIc that are shown with single and dashed lines is a double bond and one or more of $R_4'$, $R_8'$, $R_{10}'$, and $R_{11}'$ is absent, such that normal valences of carbon atoms in the rings are satisfied.

The present invention additionally comprises compounds, as follows, i.e., according to structural formulae IVa, IVb or IVc or a pharmaceutically available salt, solvate, or hydrate thereof wherein:

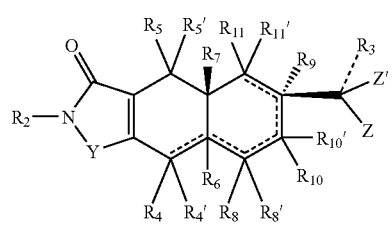

IVa

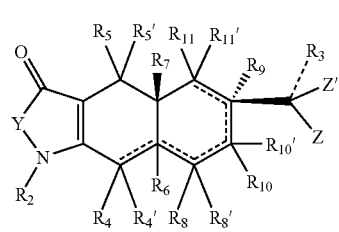

IVb

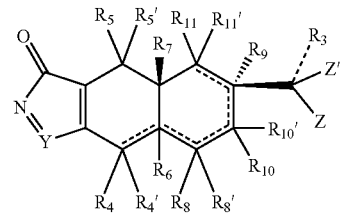

IVc

Y is nitrogen, and in structures IVa and IVb, Y can also be oxygen;

Z is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, fluoro, chloro, bromo, iodo, thio, hydroxyl, thio, heteroaryl, substituted heteroaryl, heteroalkyl, substituted heteroalkyl, heteroarylalkyl, substituted heteroarylalkyl, or is absent;

Z' is hydrogen, or is absent;

$R_2$ is present in IVa and IVb, but not IVc, and is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m$W, —CR=CR'W, =CRW, or C≡CW, wherein m=0-10;

R and R' is each independently hydrogen, cyano, nitro, halo, thio, carboxy, hydroxyl, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, substituted alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, hydroxyl, thio, or is absent;

the bond in formulae IVa, IVb and IVc that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IVa, IVb and IVc that are shown with single and dashed lines is a double bond and one or more of $R_4'$, $R_8'$, $R_9$, $R_{10}'$, and $R_{11}'$ is absent, such that normal valences of carbon atoms in the rings are satisfied.

In a second aspect, the present invention provides compositions of compounds of the invention. The compositions generally comprise one or more compounds of the invention, pharmaceutically acceptable salts, hydrates or solvates thereof, and a pharmaceutically acceptable diluent, carrier, excipient and adjuvant. The choice of diluent, carrier, excipient and adjuvant will depend upon, among other factors, the desired mode of administration.

In a third aspect, the present invention provides methods for treating or preventing prostate cancer, benign prostatic hyperplasia, reproductive disorders, and male hypogonadism. The methods generally involve administering to a patient in need of such treatment or prevention a therapeutically effective amount of a compound and/or composition of the invention.

In a fourth aspect, the current invention provides compositions for treating or preventing prostate cancer, benign prostatic hyperplasia, reproductive disorders, and male hypogonadism in a patient in need of such treatment or prevention.

In a fifth aspect the current invention provides methods for selectively modulating the activation, repression, agonism and antagonism effects of the androgen receptor in a patient. The methods generally involve administering to a patient in need of such treatment a therapeutically effective amount of a compound or composition of the invention.

In a sixth aspect, the current invention provides methods for synthesizing compounds whose formulae are given in Ia, Ib, Ia, IIb, IIIa, IIIb, IIIc, IVa, IVb, and IVc.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 depicts a number of compounds, known in the art to exhibit androgenic activity.

FIG. 6 depicts various compounds that can be synthesized according to the methods of the present invention.

FIG. 8A shows effects on LNCaP growth of each individual compound alone; FIG. 8B shows the effect in the presence of 1 nM DHT, and FIG. 8C focuses on three selected compounds (18-20), showing their effect at three concentrations in the presence of 1 nM DHT or alone.

In FIGS. 2-4, 'rt' means "room temperature."

DETAILED DESCRIPTION

Figure 2:
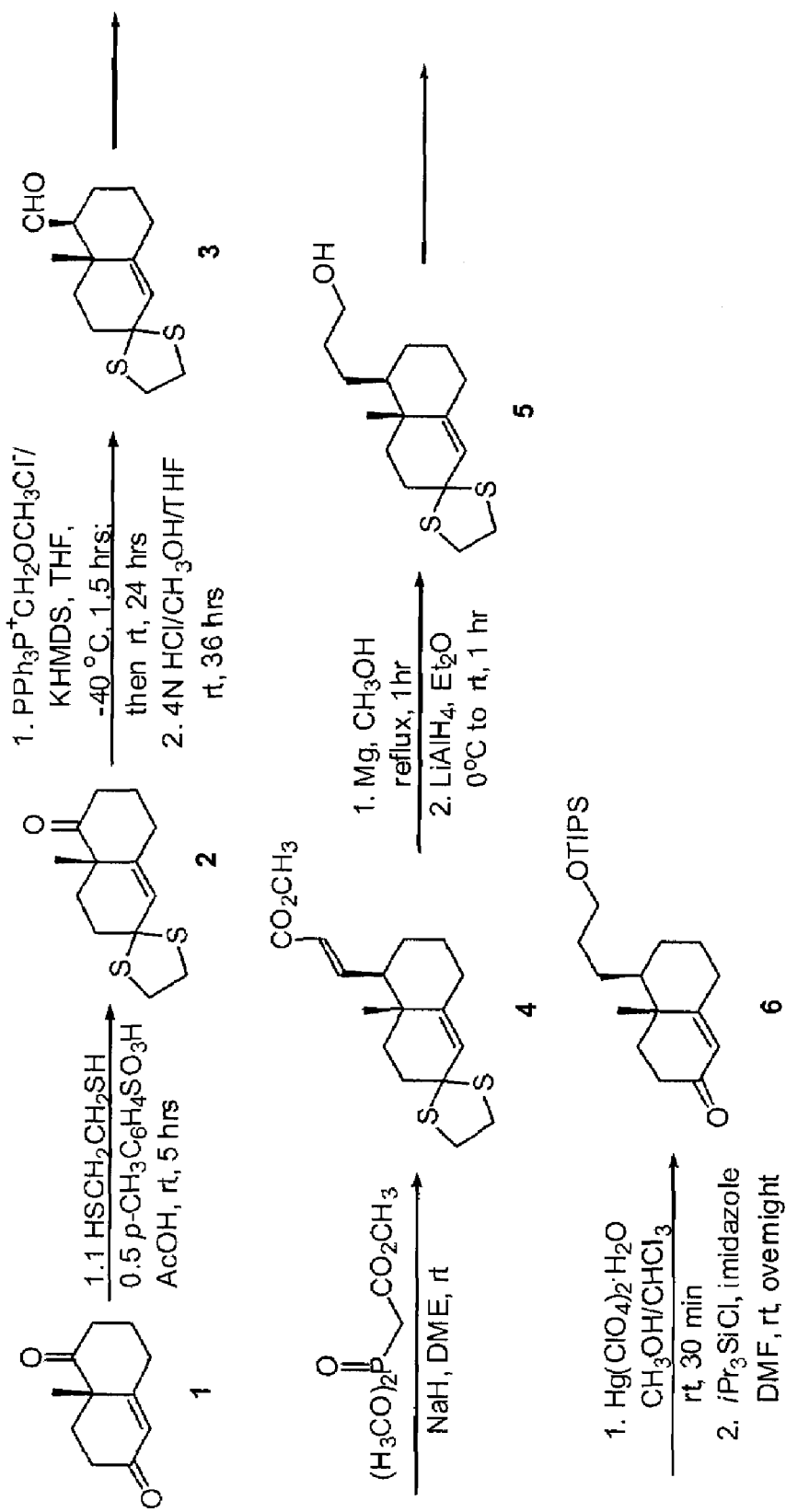
FIG. 2 depicts scheme 1 for the synthesis of a common intermediate used in synthesizing compounds of the present invention.

The non-steroidal compounds of the present invention exhibit antiandrogenic activity. Efficient methods of preparation of these compounds have been developed, and the repression of androgen receptor (AR) transcriptional activity has been demonstrated in cell culture. The compounds of the present invention can potentially be used for treatment of prostate cancer and benign prostatic hyperplasia.

Definitions

"Compounds of the invention" refers to compounds encompassed by structural Formulae Ia, Ib, Ia, IIb, IIIa, IIIb, IIIc, IVa, IVb, and IVc, disclosed herein and includes any specific compounds within those formulae whose structures are disclosed herein. The compounds of the invention may be identified either by chemical structure, or chemical name, or by both. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure), and enantiomeric and stereoisomeric mixtures, except where otherwise expressly indicated. Enantiomeric and stereoisomeric mixtures can be resolved into their component enantiomers or stereoisomers using separation techniques or chiral synthesis techniques well known to an artisan of ordinary skill. The compounds of the invention may also exist in several tautomeric forms including the enol form, the keto form and both equilibriated and non-equilibriated mixtures thereof. Accordingly, the chemical structures depicted herein encompass all possible tautomeric forms of the illustrated compounds.

The compounds of the invention also include isotopically labeled compounds where one or more atoms have an atomic mass different from the most abundant atomic mass normally found in nature for given atom. Examples of isotopes that may be incorporated into the compounds of the invention include, but are not limited to, $^2$H, $^3$H, $^{13}$C, $^{14}$C, $^{15}$N, $^{17}$O, $^{18}$O, and $^{34}$S.

Furthermore it should be understood that, when partial structures of the compounds of the invention or precursors thereto are illustrated, brackets of dashes indicate the point of attachment of the partial structure to the rest of the molecule.

"Alkyl" refers to a saturated or unsaturated, branched, straight-chain, cyclic or alicyclic, monovalent hydrocarbon radical derived by the removal of one hydrogen atom from a single carbon atom of a parent alkane, alkene or alkyne. It is to be noted, therefore, that the term alkyl also encompasses a radical derived from a cyclic moiety attached to a straight-chain, or branched chain moiety, such that the removed hydrogen atom originated with either the cyclic or acyclic portion. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, cyclopropyl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, tert-butyl, and methylene-cyclopropane, etc.; and the like.

The term "alkyl" is specifically intended to include radicals having any degree or level of saturation, i.e., groups having exclusively carbon-carbon single bonds, groups having one or more carbon-carbon double bonds, groups having one or more carbon-carbon triple bonds and groups having mixtures of single, double and triple carbon-carbon bonds. Where a specific level of saturation or unsaturation is intended, the expressions "alkanyl", "alkenyl", and "alkynyl" are used. Preferably, an alkyl group comprises from 1 to 20 carbon atoms, more preferably from 1 to 10 carbon atoms or still more preferably from 1 to 6 carbon atoms.

"Alkanyl" refers to a saturated branched, straight-chain or cyclic alkyl radical derived by the removal of one hydrogen atom from a single carbon atom of a parent alkane which itself may be linear, branched, cyclic, or contain a ring. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond, derived by the removal of one hydrogen atom from a single carbon atom of a parent alkene which itself may be linear, branched, cyclic, or contain a ring. The various groups attached to the double bond(s) may be in either the cis or trans (or E, or Z) conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; penta-2,4-diene, and the like.

"Alkynyl" refers to an unsaturated branched, straight-chain or cyclic alkyl radical having at least one carbon-carbon triple bond, derived by the removal of one hydrogen atom from a single carbon atom of a parent alkyne which itself may be linear, branched, cyclic, or contain a ring. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(=O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl, and the like.

"Acylamino" refers to a radical —NR'C(=O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino, and the like.

"Alkylamino" means a radical —NHR where R represents an alkyl or cycloalkyl group as defined herein. Representative examples include, but are not limited to, methylamino, ethylamino, 1-methylethylamino, cyclohexylamino, and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy, and the like.

"Alkoxycarbonyl" refers to a radical —C(=O)-alkoxy where alkoxy is as defined herein.

"Alkylsulfonyl" refers to a radical —S(=O)$_2$R where R is an alkyl or cycloalkyl group as defined herein. Representative examples include, but are not limited to, methylsulfonyl, ethylsulfonyl, propylsulfonyl, butylsulfonyl, and the like.

"Alkylsulfinyl" refers to a radical —S(=O)R where R is an alkyl or cycloalkyl group as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein. Representative examples include, but are not limited to, methylthio, ethylthio, propylthio, butylthio, and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from fused ring systems that comprise one or more aromatic rings, or conjugated ring systems, such as aceanthrylene, acenaphthylene, acephenanthrylene, anthracene, azulene, benzene, chrysene, coronene, fluoranthene, heptaphene, hexacene, hexaphene, as-indacene, s-indacene, indene, naphthalene (hexalene), octacene, octaphene, octalene, ovalene, pentacene, pentalene, pentaphene, perylene, phenalene, phenanthrene, picene, pleiadene, pyrene, pyranthrene, rubicene, tetraphenylene, triphenylene, trinaphthalene and the like. Additionally, aryl groups include fused ring systems containing at least one aromatic ring and at least one partially saturated ring, such as fluorene, indane, biphenylene and the like. Preferably, an aryl group comprises from 6 to 20 carbon atoms, more preferably between 6 to 12 carbon atoms.

"Arylalkyl" refers to an alkyl radical in which one of the hydrogen atoms bonded to a carbon atom, typically a terminal or sp hybridized carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). More preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylalkyloxy" refers to an —O-arylalkyl radical where arylalkyl is as defined herein.

"Aryloxycarbonyl" refers to a radical —C(=O)—O-aryl where aryl is as defined herein.

"Carbamoyl" refers to the radical —C(=O)N(R)$_2$ where each R group is independently hydrogen, alkyl, cycloalkyl or aryl as defined herein, and in the case of a substituted carbamoyl, each R may be optionally substituted as defined herein.

"Carboxy" means the radical —C(=O)OH.

"Cyano" means the radical —CN.

"Cyanate" means the group —CNO.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group is C$_3$-C$_{10}$ cycloalkyl, more preferably C$_3$-C$_7$ cycloalkyl.

"Cycloheteroalkyl" refers to a saturated or unsaturated cyclic alkyl radical in which one or more carbon atoms (and any hydrogen atoms directly bonded thereto) are independently replaced with the same or different heteroatom. Typical heteroatoms to replace the carbon atom(s) include, but are not limited to, N, P, O, S, Se, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" refers to a radical —C(=O)—OR where R is cycloheteroalkyl as defined herein.

"Dialkylamino" means a radical —NRR' where R and R' independently represent an alkyl or cycloalkyl group as defined herein. Representative examples include, but are not limited to dimethylamino, methyl-ethylamino, di-(1-methylethyl)amino, cyclohexyl-methyl amino, cyclohexyl-ethyl amino, cyclohexyl-propyl amino, and the like.

"Halo" means fluoro, chloro, bromo, or iodo.

"Heteroalkyloxy" means an —O-heteroalkyl radical where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced by the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, wherein R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group has from 5-20 non-hydrogen atoms, with 5-10 non-hydrogen atoms being particularly preferred. Preferred heteroaryl groups are those derived from thiophene, pyrrole, benzothiophene, benzofuran, indole, pyridine, pyrimidine, quinoline, imidazole, oxazole and pyrazine.

"Heteroaryloxycarbonyl" refers to a radical —C(=O)—OR where R is heteroaryl as defined herein.

"Heteroarylalkyl" refers to an acyclic alkyl radical in which one of the hydrogen atoms bonded to a carbon atom, typically a terminal or $sp^3$ hybridized carbon atom, is replaced with a heteroaryl group. Where specific alkyl moieties are intended, the nomenclature heteroarylalkanyl, heteroarylalkenyl and/or heterorylalkynyl is used. Preferably, the heteroarylalkyl radical has 6-30 non-hydrogen atoms, e.g., the alkanyl, alkenyl or alkynyl moiety of the heteroarylalkyl is $C_{1-10}$ and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Isocyano" means the group —NC.

"Isocyanate" means the group —NCO.

"Oxo" means the divalent radical =O.

"Perfluoro" means an alkyl group in which every hydrogen atom has been replaced by a fluorine atom.

"Prodrug" refers to a pharmacologically inactive derivative of a drug molecule that requires a transformation within the body to release the active drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo. Ideally, the promoiety is rapidly cleared from the body upon cleavage from the prodrug.

"Protecting group" refers to a grouping of atoms that when attached to a reactive group in a molecule masks, reduces or prevents that reactivity. Examples of protecting groups can be found in Green et al., "Protective Groups in Organic Synthesis", T. W. Greene, and P. G. M. Wuts, (Wiley, 3$^{rd}$ ed. 1999), and Harrison et al., "Compendium of Synthetic Organic Methods", Vols. 1-12 (John Wiley & Sons, 1971-2004). Representative amino protecting groups include, but are not limited to, formyl, acetyl, trifluoroacetyl, benzyl, benzyloxycarbonyl" ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are each independently replaced with the same or different substituent(s). Typical substituents include, but are not limited to, —X, —R$^{14}$, —O$^-$, =O, —OR$^{14}$, —SR$^{14}$, —S$^-$, =S, —NR$^{14}$R$^{15}$, =NR$^{14}$, —CX$_3$, —CF$_3$, —CN, —OCN, —SCN, —NO, —NO$_2$, =N$_2$, —N$_3$, —N$^+$≡C$^-$, —S(O)$_2$O$^-$, —S(O)$_2$OH, —S(O)$_2$R$^{14}$, —OS(O$_2$)O$^-$, —OS(O)$_2$R$^{14}$, —P(O)(O$^-$)$_2$, —P(O)(OR$^{14}$)(O$^-$), —OP(O)(OR$^{14}$)(OR$^{15}$), C(O)R$^{14}$, —C(S)R$^{14}$, —C(O)OR$^{14}$, —C(O)NR$^{14}$R$^{15}$, —C(O)O$^-$, —C(S)OR$^{14}$, —NR$^{16}$C(O)NR$^{14}$R$^{15}$, —NR$^{16}$C(S)NR$^{14}$R$^{15}$, —NR$^{17}$C(NR$^{16}$)NR$_{14}$R$^{15}$ and C(NR$^{16}$)NR$_{14}$R$^{15}$, where each X is independently a halogen; each R$^{14}$, R$^{15}$, R$^{16}$ and R$^{17}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{18}$R$^{19}$, —C(O)R$^{18}$ or —S(O)$_2$R$^{18}$ or optionally R$^{18}$ and R$^{19}$ together with the atom to which they are both attached form a cycloheteroalkyl or substituted cycloheteroalkyl ring; and R$^{18}$ and R$^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Thio" means the radical —SH.

"Valence" refers to the number of electrons that an atom has available to form bonds. Ordinarily in organic chemistry, no unpaired electrons are associated with an atom in its normal valence when bonded in a chemically stable molecule. A bond is formed when a pair of electrons is formally shared between two atoms. Thus, for example, the normal valences of the commonly encountered elements in organic molecules are as follows: carbon is 4, hydrogen is 1, nitrogen is 3, oxygen is 2, sulfur is 2, and the halogens each have a normal valence of 1. A carbon atom can satisfy its normal valence by forming the following combinations of bonds: 4 single bonds; two single bonds and a double bond; a triple bond and a single bond; two aromatic bonds and a single bond; or three aromatic bonds. Other combinations are also possible.

The Compounds of the Invention

The compounds of the invention include compounds of formulae Ia, Ib, IIa, IIb, IIIa, IIIb, IIIc, IVa, IVb, or IVc:

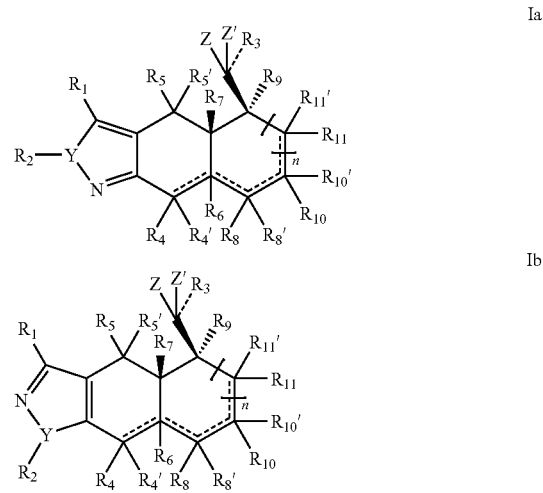

In particular, the compounds of the present invention have structural formulae Ia or Ib, or a pharmaceutically available salt, solvate, or hydrate thereof wherein:

Y is nitrogen or oxygen, and when Y is oxygen, R$_2$ is absent;

Z is hydrogen, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, chloro, bromo, iodo, thio, heteroaryl, substituted heteroaryl, heteroalkyl, substituted heteroalkyl, heteroarylalkyl, substituted heteroarylalkyl, or is absent;

$Z'$ is hydrogen, or is absent;

n is 0, 1, or 2;

$R_1$ is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroaryl, substituted heteroaryl, heteroalkyl, substituted heteroalkyl, heteroarylalkyl, or substituted heteroarylalkyl;

$R_2$ is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m W$, —CR=CR'W, =CRW, or C≡CW, wherein m=1-10;

R and R' is each independently hydrogen, cyano, nitro, halo, thio, carboxy, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, or thio;

the bond in formulae Ia and Ib that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae Ia and Ib that are shown with single and dashed lines is a double bond and one or more of $R_4'$, $R_8'$, $R_{10}'$, and $R_{11}'$ is absent, such that normal valences of carbon atoms in the rings are satisfied.

Furthermore, the compounds of the present invention have structural formulae IIa or IIb, or a pharmaceutically available salt, solvate, or hydrate thereof wherein:

Y is nitrogen or oxygen, and when Y is oxygen, $R_2$ is absent;

Z is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, fluoro, chloro, bromo, iodo, thio, hydroxyl, thio, heteroaryl, substituted heteroaryl, heteroalkyl, substituted heteroalkyl, heteroarylalkyl, substituted heteroarylalkyl, or is absent;

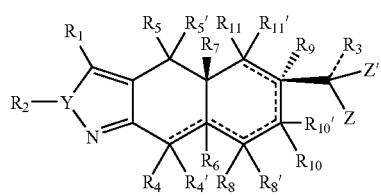

IIa

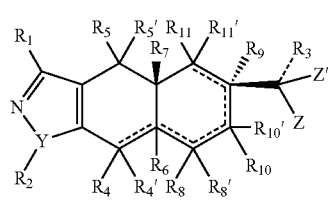

IIb

Z' is hydrogen, or is absent;

$R_1$ is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroaryl, substituted heteroaryl, heteroalkyl, substituted heteroalkyl, heteroarylalkyl, or substituted heteroarylalkyl;

$R_2$ is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m W$, —$CR$=$CR'W$, =$CRW$, or $C$≡$CW$, wherein m=0-10;

R and R' is each independently hydrogen, cyano, nitro, halo, thio, carboxy, hydroxyl, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, substituted alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, hydroxyl, thio, or is absent;

the bond in formulae IIa and IIb that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IIa and IIb that are shown with single and dashed lines is a double bond and one or more of $R_4'$, $R_8'$, $R_9$, $R_{10}'$, and $R_{11}'$ is absent, such that normal valences of carbon atoms in the rings are satisfied.

The present invention still further includes compounds according to structural formulae IIIa, IIIb or IIIc, or a pharmaceutically available salt, solvate, or hydrate thereof wherein:

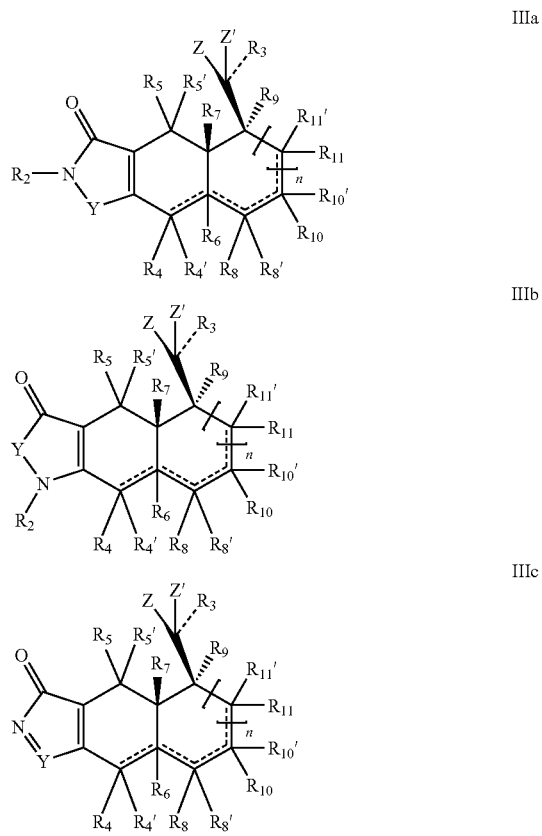

Y is nitrogen, and in structures IIIa and IIIb, Y can also be oxygen;

Z is hydrogen, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, chloro, bromo, iodo, thio, heteroaryl, substituted heteroaryl, heteroalkyl, substituted heteroalkyl, heteroarylalkyl, substituted heteroarylalkyl, or is absent;

Z' is hydrogen, or is absent;

n is 0, 1, or 2;

$R_2$ is present in IIIa and IIIb, but not IIIc, and is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is —$(CRR')_m W$, —CR=CR'W, =CRW, or C≡CW, wherein m=1-10;

R and R' is each independently hydrogen, cyano, nitro, halo, thio, carboxy, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, or thio;

the bond in formulae IIIa, IIIb and IIIc that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IIIa, IIIb and IIIc that are shown with single and dashed lines is a double bond and one or more of $R_4'$, $R_8'$, $R_{10}'$, and $R_{11}'$ is absent, such that normal valences of carbon atoms in the rings are satisfied.

The present invention additionally comprises compounds according to structural formulae IVa, IVb or IVc, or a pharmaceutically available salt, solvate, or hydrate thereof wherein:

Y is nitrogen, and in structures IVa and IVb, Y can also be oxygen;

Z is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, fluoro, chloro, bromo, iodo, thio, hydroxyl, thio, heteroaryl, substituted heteroaryl, heteroalkyl, substituted heteroalkyl, heteroarylalkyl, substituted heteroarylalkyl, or is absent;

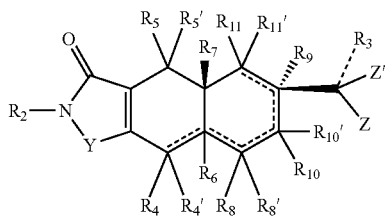

IVa

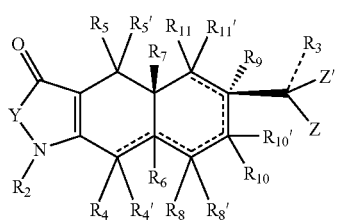

IVb

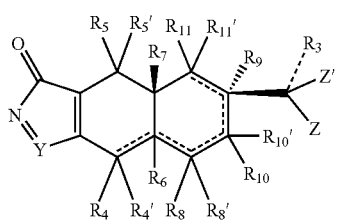

IVc

Z' is hydrogen, or is absent;

$R_2$ is present in IVa and IVb, but not IVc, and is hydrogen, alkyl, substituted alkyl, perfluoro alkyl, acyl, substituted acyl, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, heteroaryl, substituted heteroaryl, heteroalkyl, substituted heteroalkyl, heteroarylalkyl, or substituted heteroarylalkyl;

$R_3$ is $-(CRR')_m W$, $-CR=CR'W$, $=CRW$, or $C\equiv CW$, wherein m=0-10;

R and R' is each independently hydrogen, cyano, nitro, halo, thio, carboxy, hydroxyl, alkyl, substituted alkyl, aryl, substituted aryl, arylalkyl, substituted arylalkyl, heteroarylalkyl, or substituted heteroarylalkyl; and wherein W is alkyl, substituted alkyl, aryl, substituted aryl, carbamoyl, substituted carbamoyl, carboxy, cyano, heteroaryl, substituted heteroaryl, heteroalkyl, substituted heteroalkyl, heteroarylalkyl, substituted heteroarylalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl or substituted heteroarylalkyl;

each of $R_4'$, $R_8'$, $R_{10}'$, and $R_{11}'$ is independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, substituted heteroalkyl, heteroarylalkyl, substituted heteroarylalkyl, or when attached to a ring carbon atom that itself is bonded to an adjacent ring carbon atom by a double bond, is absent;

or $R_4$ and $R_4'$ together are oxo when attached to a ring carbon atom that itself is bonded to adjacent ring carbon atoms only by a single bond;

or $R_8$ and $R_8'$ together are oxo when attached to a ring carbon atom that itself is bonded to adjacent ring carbon atoms only by a single bond;

or $R_{10}$ and $R_{10}'$ together are oxo when attached to a ring carbon atom that itself is bonded to adjacent ring carbon atoms only by a single bond;

or $R_{11}$ and $R_{11}'$ together are oxo when attached to a ring carbon atom that itself is bonded to adjacent ring carbon atoms only by a single bond, or when n=0, $R_{11}$ and $R_{11}'$ are both absent;

$R_5$, $R_5'$, are independently hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, thio, nitro, hydroxyl, heteroaryl, substituted heteroaryl, heteroalkyl, substituted heteroalkyl, heteroarylalkyl, substituted heteroarylalkyl, or together are oxo;

$R_6$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, substituted heteroarylalkyl, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroaryl, substituted heteroaryl, heteroalkyl, substituted heteroalkyl, heteroarylalkyl, or substituted heteroarylalkyl;

$R_9$ is hydrogen, alkyl, substituted alkyl, amino, alkylamino, substituted alkylamino, dialkylamino, substituted dialkylamino, carboxy, acyl, substituted acyl, acylamino, substituted acylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, heteroaryl, substituted heteroaryl, heteroarylalkyl, substituted heteroarylalkyl, halo, hydroxyl, thio, or is absent;

the bond in formulae IVa, IVb and IVc that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae IVa, IVb and IVc that are shown with single and dashed lines is a double bond and one or more of $R_4'$, $R_8'$, $R_9$, $R_{10}'$, and $R_{11}'$ is absent, such that normal valences of carbon atoms in the rings are satisfied.

It is to be understood that, in formulae Ia, Ib, IIa, IIb, IIIa, IIIb, IIIc, IVa, IVb, and IVc, group $R_7$ has the exact stereochemistry shown, i.e., $R_7$ points out of the plane of the paper.

It is further to be understood that, in formulae Ia, Ib, IIIa, IIIb, and IIIc, the group to which Z, Z' and $R_3$ is attached has the exact stereochemistry shown, i.e., it points out of the plane of the paper. Correspondingly, group $R_9$ points down into the plane of the paper in those structures.

Preferred compounds of the present invention are any of those having formulae Ia, Ib, IIa, IIb, IIIa, IIIb, IIIc, IVa, IVb, or IVc, and having choices of substituents, and formulae of substituents, in any combination, as follows.

Preferably, n=1.

Preferably, Y is nitrogen.

Preferably Z is hydrogen.

Preferably, Z' is hydrogen.

Preferably, $R_1$ is hydrogen, alkyl, substituted alkyl, or perfluoro alkyl; and even more preferably, $R_1$ is hydrogen or alkyl having 6 carbon atoms or fewer; and still more preferably, $R_1$ is hydrogen.

Preferably, $R_2$ is hydrogen, alkyl, substituted alkyl, perfluoro alkyl, acyl, substituted acyl, alkoxycarbonyl, substituted alkoxycarbonyl, aryl, substituted aryl, arylalkyl, or substituted arylalkyl. More preferably, $R_2$ is hydrogen, alkyl, or substituted alkyl, perfluoro alkyl. Even more preferably, $R_2$ is hydrogen or alkyl having 6 carbon atoms or fewer; and still more preferably, $R_2$ is hydrogen.

Preferably, $R_3$ is —$(CRR')_m$W, or —CR=CR'W.

However, regardless of the form of $R_3$, where applicable m is preferably 0-6, more preferably 1-6, still more preferably 0-3, and yet more preferably 1-3, and even more preferably 0 or 1.

Furthermore, and also regardless of the form of $R_3$, where applicable R and R' are each independently hydrogen, halo, alkyl, or substituted alkyl.

Still further, W is preferably alkyl, substituted alkyl, aryl, substituted aryl, carbamoyl, or substituted carbamoyl, and still more preferably alkyl or substituted alkyl, and even more preferably alkyl or substituted alkyl having 6 carbon atoms or fewer, and even more preferably methyl or substituted methyl.

Each of $R_4$, $R_8$, $R_{10}$, and $R_{11}$ is preferably independently hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, or substituted heteroalkyl.

Each of $R_4$, $R_8$, $R_{10}$, and $R_{11}$ is more preferably independently hydrogen, alkyl, substituted alkyl, amino, aryl, substituted aryl, carboxy, cyano, nitro, halo, thio, or hydroxyl.

Each of $R_4$, $R_8$, $R_{10}$, and $R_{11}$ is even more preferably independently hydrogen, alkyl, or substituted alkyl.

Each of $R_4$, $R_8$, $R_{10}$, and $R_{11}$ is still more preferably independently hydrogen, or alkyl having 6 carbon atoms or fewer.

Each of $R_4$, $R_8$, $R_{10}$, and $R_{11}$ is yet more preferably independently hydrogen.

Each of $R_4'$, $R_8'$, $R_{10}'$, and $R_{11}'$ is preferably independently hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, or substituted heteroalkyl.

Each of $R_4'$, $R_8'$, $R_{10}'$, and $R_{11}'$ is more preferably independently hydrogen, alkyl, substituted alkyl, amino, aryl, substituted aryl, carboxy, cyano, nitro, halo, thio, or hydroxyl.

Each of $R_4'$, $R_8'$, $R_{10}'$, and $R_{11}'$ is even more preferably independently hydrogen, alkyl, or substituted alkyl.

Each of $R_4'$, $R_8'$, $R_{10}'$, and $R_{11}'$ is still more preferably independently hydrogen, or alkyl having 6 carbon atoms or fewer.

Each of $R_4'$, $R_8'$, $R_{10}'$, and $R_{11}'$ is yet more preferably independently hydrogen.

Each of $R_5$, $R_5'$ is preferably independently hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, substituted heteroalkyl, or together are oxo.

Each of $R_5$, $R_5'$ is more preferably independently hydrogen, alkyl, substituted alkyl, amino, aryl, substituted aryl, carboxy, cyano, nitro, halo, thio, or hydroxyl.

Each of $R_5$, $R_5'$ is even more preferably independently hydrogen, alkyl, or substituted alkyl.

Each of $R_5$, $R_5'$ is still more preferably independently hydrogen, or alkyl having 6 carbon atoms or fewer.

Each of $R_5$, $R_5'$ is yet more preferably independently hydrogen.

When present, $R_6$ is preferably hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, or substituted heteroalkyl.

When present, $R_6$ is more preferably hydrogen, alkyl, substituted alkyl, amino, aryl, substituted aryl, carboxy, cyano, nitro, halo, thio, or hydroxyl.

When present, $R_6$ is even more preferably hydrogen, alkyl, or substituted alkyl.

When present, $R_6$ is still more preferably hydrogen, or alkyl having 6 carbon atoms or fewer.

When present, $R_6$ is yet more preferably hydrogen.

$R_7$ is preferably hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, or substituted heteroalkyl.

$R_7$ is more preferably hydrogen, alkyl, substituted alkyl, amino, aryl, substituted aryl, carboxy, cyano, nitro, halo, thio, or hydroxyl.

$R_7$ is even more preferably hydrogen, alkyl, or substituted alkyl.

$R_7$ is still more preferably hydrogen, or alkyl having 6 carbon atoms or fewer.

$R_7$ is yet more preferably methyl.

$R_9$ is preferably hydrogen, alkyl, substituted alkyl, alkoxy, substituted alkoxy, amino, alkylamino, substituted alkylamino, aryl, substituted aryl, arylalkyl, substituted arylalkyl, carboxy, cyano, nitro, halo, thio, hydroxyl, heteroalkyl, or substituted heteroalkyl.

$R_9$ is more preferably hydrogen, alkyl, substituted alkyl, amino, aryl, substituted aryl, carboxy, cyano, nitro, halo, thio, or hydroxyl.

$R_9$ is even more preferably hydrogen, alkyl, or substituted alkyl.

$R_9$ is still more preferably hydrogen, or alkyl having 6 carbon atoms or fewer.

$R_9$ is yet more preferably methyl.

The bond between the two carbon atoms to which $R_6$ and the pair $R_4$ and $R_4'$ are bonded is preferably a double bond, and one of $R_4$ and $R_4'$ is absent.

The bond between the two carbon atoms to which $R_6$ and the pair $R_8$ and $R_8'$ are bonded is preferably a single bond.

The bond between the two carbon atoms to which the pair $R_{10}$ and $R_{10}'$ and the pair $R_8$ and $R_8'$ are bonded is preferably a single bond.

The bond between the two carbon atoms to which the pair $R_{10}$ and $R_{10}'$ and the pair $R_{11}$ and $R_{11}'$ are bonded is preferably a single bond.

In structures of formulae IIa, IIb, IVa, IVb, and IVc, the bond between the two carbon atoms to which $R_9$ and the pair $R_{11}$ and $R_{11}'$ are bonded is preferably a double bond, and one of $R_{11}$ and $R_{11}'$ is absent, and $R_9$ is absent.

It is also consistent with the present invention that none of $R_4$, $R_8$, $R_{10}$, and $R_{11}$, $R_4'$, $R_8'$, $R_{10}'$, and $R_{11}'$, $R_5$, $R_5'$, $R_6$, $R_7$ and $R_9$ is aryl or substituted aryl.

Synthesis of the Compounds of the Invention

Figure 3:
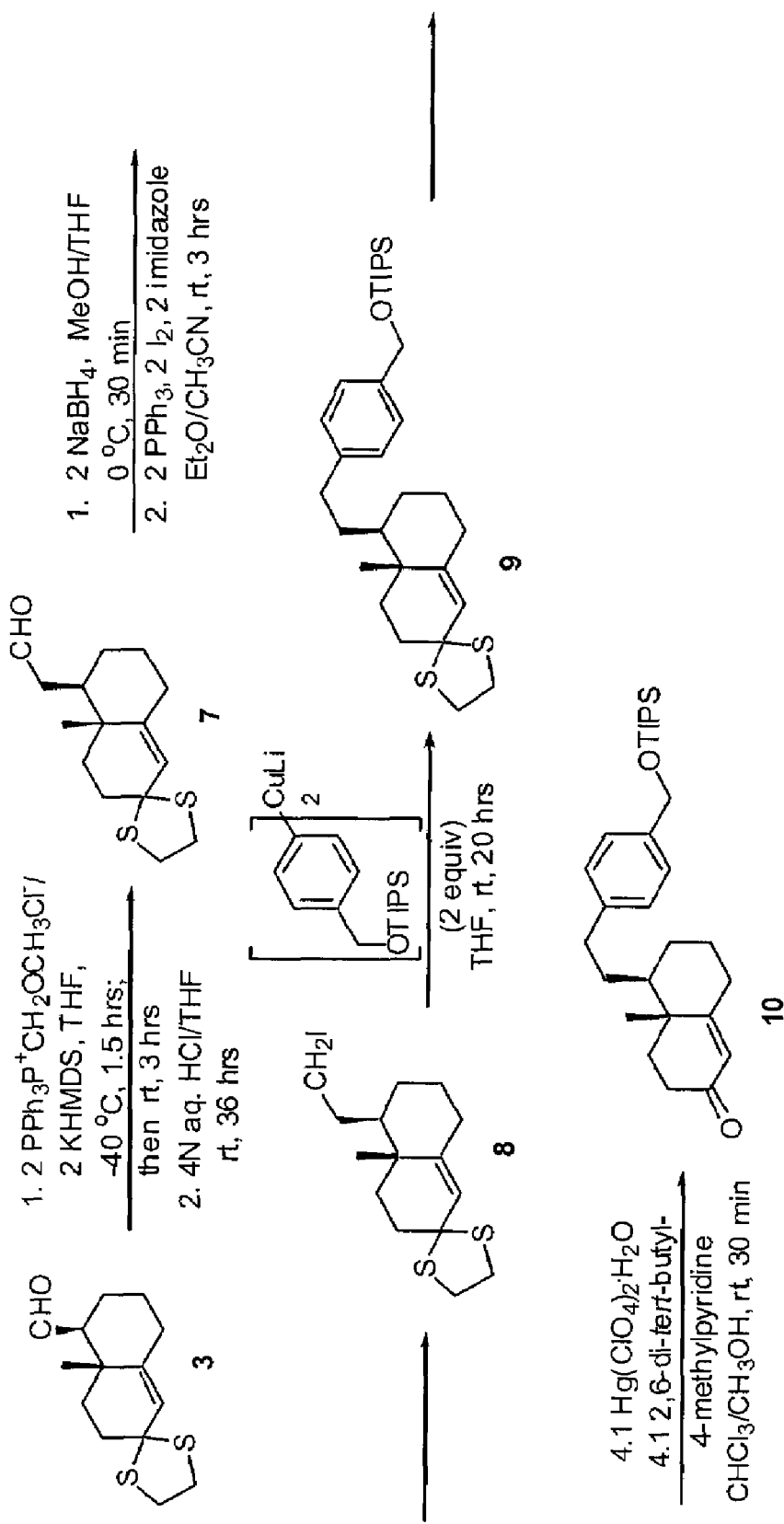
FIG. 3 depicts scheme 2 for the synthesis of a common intermediate used in synthesizing compounds of the present invention.
Figure 4:
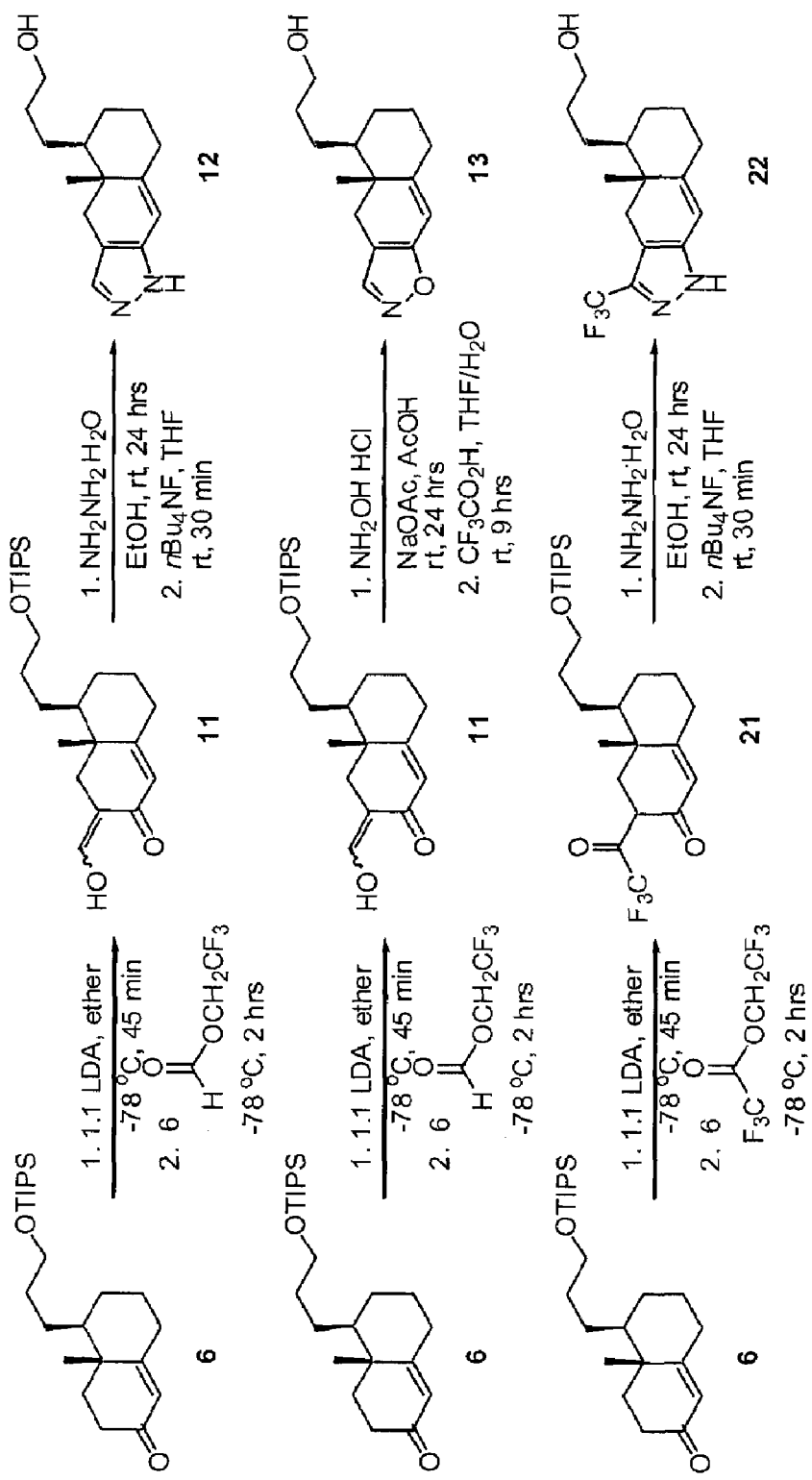
FIG. 4 depicts representative examples of scheme 3 for heterocycle formation in synthesizing compounds of the present invention.

The compounds of the invention of formulae Ia, Ib, IIIa, IIIb, and IIIc may be obtained via the synthetic methods illustrated in FIGS. 2-4, respectively. Starting materials useful for preparing compounds of the invention and intermediates thereof are commercially available or can be prepared by well-known synthetic methods. Other methods for synthesis of the compounds described herein are either described in the art or will be readily apparent to the skilled artisan in view of general references well-known in the art (see e.g., Green et al., "Protective Groups in Organic Chemistry", (Wiley, 2nd ed. 1991); Harrison et al., "Compendium of Synthetic Organic Methods", Vols. 1-8 (John Wiley and Sons, 1971-1996); "Beilstein Handbook of Organic Chemistry", Beilstein Institute of Organic Chemistry, Frankfurt, Germany; Feiser et al., "Reagents for Organic Synthesis", Volumes 1-17, Wiley Interscience; Trost et al., "Comprehensive Organic Synthesis", Pergamon Press, 1991; "Theilheimer's Synthetic Methods of Organic Chemistry", Volumes 1-45, Karger, 1991; March, "Advanced Organic Chemistry", Wiley Interscience, 1991; Larock "Comprehensive Organic Transformations", VCH Publishers, 1989; Paquette, "Encyclopedia of Reagents for Organic Synthesis", John Wiley & Sons, 1995) and may be used to synthesize the compounds of the invention. Further, specific references for synthesizing indans, and decalins are easily accessible to the ordinarily skilled artisan. Accordingly, the methods presented in the schemes herein are illustrative rather than comprehensive.

Compounds depicted in FIGS. 2-4 are compounds of structural formulae Ia, Ib, IIIa, IIIb, IIIc or precursors thereof. Those of ordinary skill in the art will appreciate that the synthetic steps illustrated in FIGS. 2-4 are also applicable to the preparation of many other compounds of structural formulae Ia, Ib, IIIa, IIIb, or IIIc.

Two panels of molecules with various heterocycles, variously substituted, on the left-hand side and a fixed right hand side were synthesized. Two scaffolds with different right hand sides were considered; in the first set, the right-hand side has a bulky extension comprising a phenyl group, exemplified by compounds 18-20 in FIG. 5; in the second set, the right-hand side consists of just a three-carbon chain with a terminal hydroxy-group, exemplified by compounds 14-17 and 22-23, in FIG. 5. Both sets of compounds have a terminal hydroxyl group on their right-hand side substituent.

Efficient syntheses of both scaffolds were developed. The precursors for the synthesis of heterocycles 6 (FIG. 2) and 10 (FIG. 3) are prepared from Weiland-Miescher ketone 1 in 7 steps in 14% and 13% overall yields, respectively. Both syntheses are efficient and afford gram quantities of the desired intermediates. Heterocycles are then formed from these precursors via a three-step sequence (FIG. 4) in 10-40% yields.

It would further be understood by one of ordinary skill in the art of synthetic organic chemistry that synthetic methods employed to make compounds of formulae Ia and Ib can readily be adapted to synthesize compounds of formulae IIa and IIb, as well as IVa, IVb, and IVc.

Therapeutic Uses of the Compounds of the Invention

In accordance with the present invention, a compound and/or composition of the invention is administered to a patient, preferably a human, suffering from diseases mediated by the androgen receptor, which include but are not limited to, prostate cancer, androgen insensitivity syndromes (AIS), benign prostatic hyperplasia, and spinal and bulbar muscular atrophy. Further, in certain embodiments, the compounds and/or compositions of the invention are administered to a patient, preferably a human, as a preventative measure against various diseases or disorders. Thus, the compounds and/or compositions of the invention may be administered as a preventative measure to a patient having a predisposition which includes, but is not limited to, prostate cancer, androgen insensitivity syndromes (AIS), benign prostatic hyperplasia, and spinal and bulbar muscular atrophy. Accordingly, the compounds and/or compositions of the invention may be used for the prevention of one disease or disorder and concurrently treating another (e.g., preventing AIS and treating prostate cancer).

Procedures for treating diseases, which include but are not limited to, prostate cancer, androgen insensitivity syndromes (AIS), benign prostatic hyperplasia, and spinal and bulbar muscular atrophy with prior art compounds have been described in the art. Thus, those of ordinary skill in the art may readily assay and use the compounds and/or compositions of structural Formulae Ia, Ib, IIa, IIb, IIIa, IIIb, IIIc, IVa, IVb, and IVc to treat diseases, which include but are not limited to, prostate cancer, androgen insensitivity syndromes (AIS), benign prostatic hyperplasia, and spinal and bulbar muscular atrophy.

Therapeutic/Prophylactic Administration

The compounds and/or compositions of the invention may be advantageously used in human medicine. As previously described in the preceding section, compounds and compositions of the invention are useful for the treatment or prevention of diseases, which include, but are not limited to, prostate cancer, androgen insensitivity syndromes (AIS), benign prostatic hyperplasia, and spinal and bulbar muscular atrophy.

When used to treat or prevent disease or disorders, compounds and/or compositions of the invention may be administered or applied singly, or in combination with other agents. The compounds and/or compositions of the invention may also be administered or applied singly, or in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal and most preferably a human.

The present compounds and/or compositions of the invention, which comprise one or more compounds of the invention, are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectal, by inhalation, or topical, particularly to the ears, nose, eyes, or skin. The preferred mode of administration is left to the discretion of the practitioner, and will depend in-part upon the site of the medical condition. In most instances, administration will result in the release of the compounds and/or compositions of the invention into the bloodstream.

In specific embodiments, it may be desirable to administer one or more compounds and/or compositions of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the disease.

In certain embodiments, it may be desirable to introduce one or more compounds and/or compositions of the invention into the central nervous system by any suitable route, including intraventricular, intrathecal and epidural injection. Intraventricular injection may be facilitated by an intraventricular catheter, for example, attached to a reservoir, such as an Ommaya reservoir.

A compound and/or composition of the invention may also be administered directly to the lung by inhalation. For administration by inhalation, a compound and/or composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide, or any other suitable gas) may be used to deliver compounds of the invention directly to the lung.

Alternatively, a Dry Powder Inhaler ("DPI") device may be used to administer a compound and/or composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the invention and a suitable powder base such as lactose or starch for these systems.

Another type of device that may be used to deliver a compound and/or composition of the invention to the lung is a liquid spray device. Liquid spray systems use extremely small nozzle holes to aerosolize liquid drug formulations that may then be directly inhaled into the lung.

In one embodiment, a nebulizer is used to deliver a compound and/or composition of the invention to the lung. Nebulizers create aerosols from liquid drug formulations by using, for example, ultrasonic energy to form fine particles that may be readily inhaled (see e.g., Verschoyle et al., *British J. Cancer*, 80, Suppl. 2, 96, (1999), which is incorporated herein by reference). Examples of nebulizers include devices supplied by Sheffield/Systemic Pulmonary Delivery Ltd. (see, Armer et al., U.S. Pat. No. 5,954,047; van der Linden et al., U.S. Pat. No. 5,950,619; van der Linden et al., U.S. Pat. No. 5,970,974), Aventis, and Batelle Pulmonary Therapeutics.

In another embodiment, an electrohydrodynamic ("EHD") aerosol device is used to deliver a compound and/or composition of the invention to the lung. EHD aerosol devices use electrical energy to aerosolize liquid drug solutions or suspensions (see e.g., Noakes et al., U.S. Pat. No. 4,765,539). EHD aerosol devices may deliver drugs to the lung more efficiently than other pulmonary delivery technologies.

In another embodiment, the compounds of the invention can be delivered in a vesicle, in particular a liposome (see Langer, *Science*, 249:1527-1533, (1990); Treat et al., in "Liposomes in the Therapy of Infectious Disease and Cancer", Lopez-Berestein and Fidler (eds.), Liss, N.Y., pp. 353-365, (1989); see generally "Liposomes in the Therapy of Infectious Disease and Cancer", Lopez-Berestein and Fidler (eds.), Liss, N.Y., (1989)).

In yet another embodiment, the compounds of the invention can be delivered via sustained release systems, preferably oral sustained release systems. In one embodiment, a pump may be used (see Langer, supra; Sefton, *CRC Crit. Ref. Biomed. Eng.*, 14:201, (1987); Saudek et al., *New Engl. J. Med.*, 321:574, (1989)).

In another embodiment, polymeric materials can be used (see "Medical Applications of Controlled Release", Langer and Wise (eds.), CRC Press, Boca Raton, Fla. (1974); "Controlled Drug Bioavailability", Drug Product Design and Performance, Smolen and Ball (eds.), Wiley, N.Y. (1984); Ranger and Peppas, *J. Macromol. Sci. Rev. Macromol. Chem.*, 23:61, (1983); see also Levy et al., *Science*, 228: 190, (1985); During et al., *Ann. Neurol.*, 25:351, (1989); Howard et al, *J. Neurosurg.*, 71:105, (1989)). In a preferred embodiment, polymeric materials are used for oral sustained release delivery. In another embodiment, enteric-coated preparations can be used for oral sustained release administration. In still another embodiment, osmotic delivery systems are used for oral sustained release administration (Verma et al., *Drug Dev. Ind. Pharm.*, 26:695-708, (2000)).

In yet another embodiment, a controlled-release system can be placed in proximity of the target of the compounds and/or composition of the invention, thus requiring only a fraction of the systemic dose (see, e.g., Goodson, in "Medical Applications of Controlled Release", supra, vol. 2, pp. 115-138 (1984)). Other controlled-release systems discussed in Langer, *Science*, 249:1527-1533, (1990), may also be used.

Compositions of the Invention

The present compositions contain a therapeutically effective amount of one or more compounds of the invention, preferably in purified form, together with a suitable amount of a pharmaceutically acceptable vehicle, so as to provide the form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that may be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see, e.g., Remington's Pharmaceutical Sciences, Philadelphia College of Pharmacy and Science, 17th Edition, 1985).

For topical administration, compounds of the invention may be formulated as solutions, gels, ointments, creams, suspensions, etc., as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In a preferred embodiment, the compounds of the invention are formulated in accordance with routine procedures as a composition adapted for intravenous administration to human beings. Typically, compounds of the invention for intravenous administration are prepared as solutions in sterile isotonic aqueous buffer. For injection, a compound of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the invention is administered by infusion, it can be dispensed, for example, with an infusion bottle containing sterile pharmaceutical grade water or saline. When the compound of the invention is administered by injection, an ampoule of sterile water for injection or saline solution can be provided so that the ingredients may be mixed prior to administration.

For transmucosal administration, penetrants appropriate to the barrier to be permeated are used in the formulation. Such penetrants are generally known to one of ordinary skill in the art.

Compositions for oral delivery may be in the form of, for example, tablets, lozenges, aqueous or oily suspensions, granules, powders, emulsions, capsules, syrups, or elixirs. Orally administered compositions may optionally contain one or more agents, for example, sweetening agents such as fructose, aspartame or saccharin; flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM, etc). Additionally, flavoring agents, preservatives, coloring agents, bile salts, acylcarnitines and the like may be added.

For buccal administration, the compositions may take the form of tablets, lozenges, etc., formulated in conventional manner.

Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see e.g., Biesalski, U.S. Pat. No. 5,112,598; Biesalski, U.S. Pat. No. 5,556,611).

A compound of the invention may also be formulated in rectal or vaginal compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention and/or compositions thereof, will generally be used in an amount effective to achieve the intended purpose. For use to treat or prevent diseases or disorders such as prostate cancer, androgen insensitivity syndromes (AIS), benign prostatic hyperplasia, and spinal and bulbar muscular atrophy, the compounds of the invention and/or compositions thereof, are administered or applied in a therapeutically effective amount.

The amount of a compound of the invention that will be effective in the treatment of a particular disorder or condition disclosed herein will depend on the nature of the disorder or condition and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds and/or compositions of the invention are delivered by oral sustained release administration. Preferably, in this embodiment, the compounds and/or compositions of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration are dependent on the potency of the compound of the invention, but are generally about 0.001 mg to about 200 mg of a compound of the invention per kilogram body weight. Dosage ranges may be readily determined by methods known to the skilled artisan.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Combination Therapy

In certain embodiments, the compounds of the invention can be used in combination therapy with at least one other therapeutic agent. The compound of the invention and the therapeutic agent can act additively or, more preferably, synergistically. In a preferred embodiment, a compound of the invention is administered concurrently with the administration of another therapeutic agent. In another preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior to or subsequent to, administration of another therapeutic agent. Other therapeutic agents which may be used with the compounds and/or compositions of the invention, include but are not limited to, drugs used to treat diseases such as prostate cancer, benign prostatic hyperplasia, reproductive disorders, male hypogonadism, androgen insensitivity syndromes, and spinal and bulbar muscular atrophy.

EXAMPLES

The invention is further defined by reference to the following examples, which describe in detail preparation of compounds and compositions of the invention and assays for using compounds and compositions of the invention. It will be apparent to those of ordinary skill in the art that many modifications, both to materials and methods, may be practiced without departing from the scope of the invention.

Figure 5:
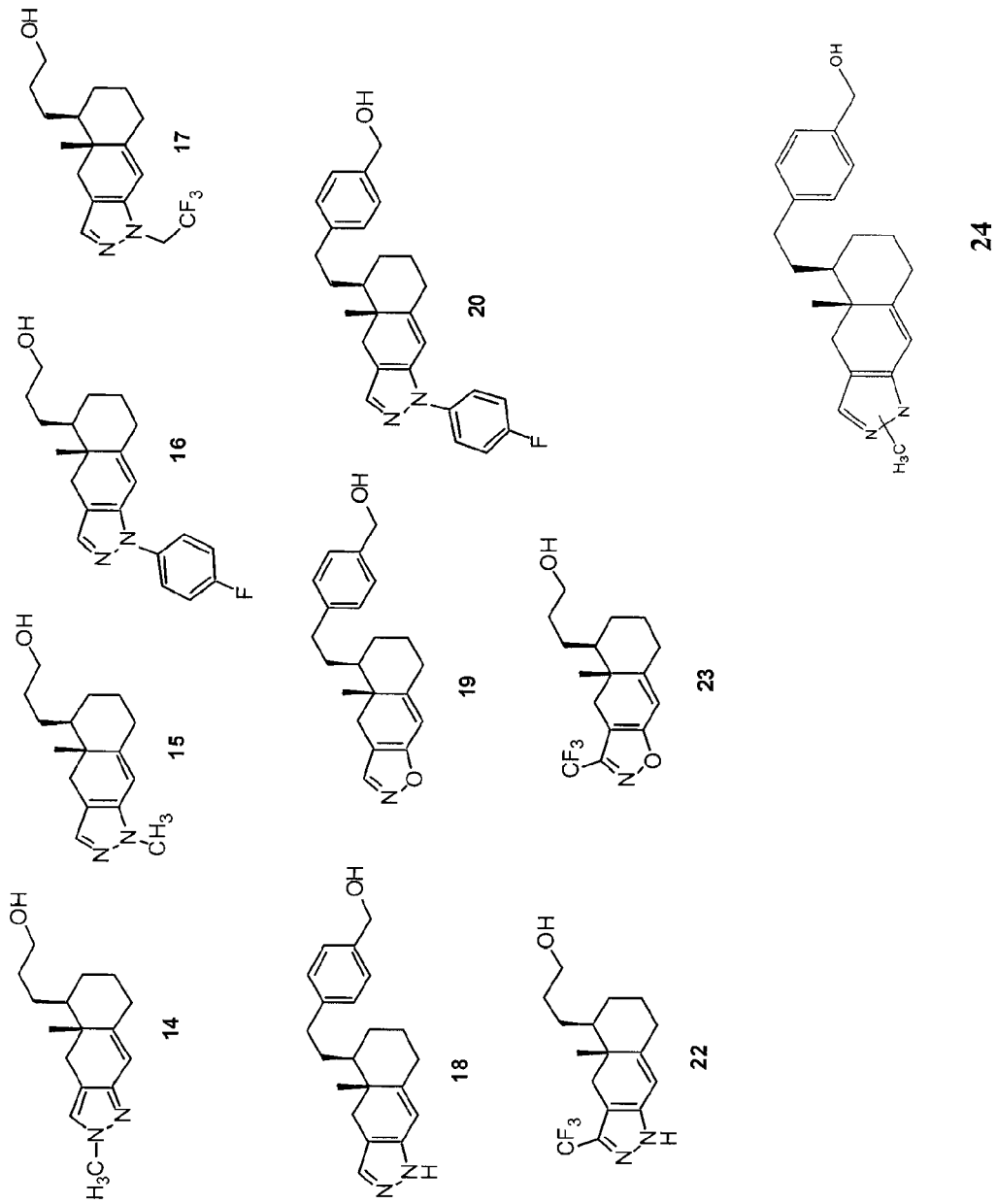
FIG. 5 depicts representative compounds synthesized according to the methods of the present invention.

Compounds in the following examples are depicted in FIG. 5 and were synthesized using one of the methods depicted in FIGS. 2-4, as further described in the experimental procedures, hereinbelow. FIGS. 2 and 3 show the synthetic routes to intermediates that were then used to synthesize the compounds 14-20, and 22-23, as shown herein. In particular, ketone 6 was used to synthesize compounds 12-17, 22, and 23. Ketone 10 was used to prepare compounds 18-20. Compounds 1, 2 and 3 in FIG. 2 were synthesized following literature procedures.

Various compounds that can also be synthesized according to the methods of the present invention are shown in FIG. 6.

Example 1

(E)-Methyl 3-(1,2,3,4,8,8α-hexahydro-8α-methyl-spiro[1',3'-dithiolane-2',6(7H)naphthalen]-1-yl)acrylate (Structure 4)

Sodium hydride (60% suspension in oil, 56 mg, 1.4 mmol) was washed with hexanes and suspended in 0.5 ml of anhydrous 1,2-dimethoxyethane. The resulting suspension was cooled to 0° C., and trimethylphosphonoacetate (319 mg, 1.75 mmol) was added dropwise over 10 min. The resulting mixture was stirred at 0° C. for 30 min., then allowed to warm up to room temperature. A solution of aldehyde 3 (268 mg, 1 mmol) in 1.5 ml of anhydrous 1,2-dimethoxyethane was added quickly. The reaction mixture was stirred at room temperature for 3.5 hrs, then quenched with water. The mixture was extracted with ether. Ethereal extracts were combined, washed with brine, dried over anhydrous $MgSO_4$, concentrated under reduced pressure. Column chromatography on silica gel afforded the desired product as a colorless oil, 204 mg (63%): $^1$H NMR ($CDCl_3$) δ 6.92 (dd, J=15.6, 8.8 Hz, 1H), 5.83 (d, J=15.6 Hz, 1H), 5.54 (s, 1H), 3.73 (s, 3H), 3.32-3.40 (m, 3H), 3.20-3.27 (m, 1H), 2.13-2.22 (m, 3H), 2.00-2.09 (m, 2H), 1.78-1.85 (m, 1H), 1.49-1.71 (m, 4H), 1.29-1.41 (m, 1H), 1.03 (s, 3H); $^{13}$C NMR ($CDCl_3$) δ 167.0, 149.8, 114.5, 125.6, 121.9, 65.7, 52.1, 51.6, 40.2, 39.7, 37.7, 37.6, 37.3, 32.0, 27.4, 26.6, 18.8.

The (Z)-isomer was isolated as a colorless oil, 14 mg (4%): $^1$H NMR ($CDCl_3$) δ 6.12 (dd, J=11.2, 10.8 Hz, 1H), 5.80 (dd, J=11.8, 0.6 Hz, 1H), 5.54 (s, 1H), 3.72 (s, 3H), 3.32-3.39 (m, 3H), 3.21-3.26 (m, 1H), 2.11-2.17 (m, 3H), 2.00-2.09 (m, 2H), 1.72-1.82 (m, 1H), 1.48-1.58 (m, 4 H), 1.07 (s, 3H).

Example 2

3-(1,2,3,4,8,8α-Hexahydro-8α-methylspiro[1',3'-dithiolane-2',6(7H)naphthalen]-1-yl)-2-propen-1-ol (Structure 5)

A solution of acrylate 4 (960 mg, 2.96 mmol) and magnesium turnings (729 mg, 30 mmol) in 20 ml of methanol was refluxed for 1.5 hrs. Then it was cooled to 0° C., and 10% aq. HCl (35 ml) was added slowly over 10 min. The resulting mixture was extracted with ether; ethereal extracts were combined, washed with brine, dried over anhydrous $MgSO_4$, and concentrated under reduced pressure to afford methyl 3-(1,2,3,4,8,8α-hexahydro-8α-methylspiro[1',3'-dithiolane-2',6 (7H)naphthalen]-1-yl)propionate as a white solid, 872 mg (90% yield): $^1$H NMR ($CDCl_3$) δ 5.51 (s, 1H), 3.67 (s, 3H), 3.23-3.40 (m, 3H), 3.20-3.25 (m, 1H), 2.36-2.44 (m, 1H), 2.09-2.25 (m, 4H), 1.96-2.03 (m, 1H), 1.82-1.91 (m, 2H), 1.74-1.80 (m, 1H), 1.56-1.66 (m, 2H), 1.29-1.41 (m, 1H), 1.18-1.31 (m, 3H), 1.05-1.09 (m, 1H), 0.96 (s, 3H); $^{13}$C NMR ($CDCl_3$) δ 174.5, 146.1, 125.0, 66.0, 51.8, 48.7, 40.2, 39.8, 38.1, 37.6, 37.0, 33.1, 32.7, 27.3, 25.2, 18.1.

The solid was dissolved in dry ether (20 ml) and cooled to 0° C. Lithium aluminum hydride (172 mg, 4.5 mmol) was added slowly over 10 min. The reaction mixture was stirred at 0° C. for 30 min, then at room temperature for 1 hr. Subsequently the reaction mixture was worked up by adding sequentially water (1 ml, very slowly), 10% aq. NaOH (2 ml), and water (3 ml). The white precipitate was filtered off, washed with ether and dichloromethane. The liquid phases were separated, and the aqueous phase was extracted with dichloromethane. Organic fractions were combined, washed with saturated aq. $NH_4Cl$, and brine, dried over anhydrous $MgSO_4$, concentrated under reduced pressure to afford desired product 5 as a colorless oil, 750 mg (85% over 2 steps): 1H NMR ($CDCl_3$) δ 5.50 (s, 1H), 3.63 (dt, J=6.4, 2.8 Hz, 2H), 3.31-3.38 (m, 3H), 3.20-3.25 (m, 1H), 2.10-2.19 (m, 3H), 1.96-2.03 (m, 1H), 1.86 (dt, J=13.2, 4.0 Hz, 1H), 1.64-1.79 (m, 3H), 1.50-1.61 (m, 2H), 1.37-1.47 (m, 2H), 1.16-1.30 (m, 2H), 0.96-1.10 (m, 2H), 0.95 (s, 3H); $^{13}$C NMR ($CDCl_3$) δ 146.5, 124.8, 66.0, 63.5, 49.1, 40.2, 39.7, 38.2, 37.6, 37.1, 32.8, 31.7, 27.6, 27.4, 25.9, 18.1. The product was used without further purification.

Example 3

4α-Methyl-5-[3-(triisopropylsilyloxy)propyl]-4,4α,5,6,7,8-hexahydro-3H-naphthalen-2-one (Structure 6)

A solution of mercury (II) perchlorate hydrate (1.67 g, 4 mmol) in 8 ml of methanol was added dropwise over 10 min to a stirred solution of alcohol 5 (527 mg, 1.76 mmol) in 10 ml of chloroform. The resulting yellow reaction mixture was stirred at room temperature for 30 min, then the precipitate was filtered off. The filtrate was treated with saturated aq. $NaHCO_3$ (10 ml), and filtered again to remove all remaining precipitate. The clear filtrate was extracted with chloroform. Organic fractions were combined, washed with brine, dried over anhydrous $MgSO_4$, concentrated under reduced pressure to afford 4α-methyl-5-[3hydroxypropyl]-4,4α,5,6,7,8-hexahydro-3H-naphthalen-2-one as a yellow oil, 286 mg (73% yield): $^1$H NMR ($CDCl_3$) δ 5.74 (s, 1H), 3.66 (t, J=6.0 Hz, 2H), 2.32-2.48 (m, 3H), 2.22-2.28 (m, 1H), 2.12 (ddd, J=13.2, 4.8, 3.4 Hz, 1H), 1.88-1.95 (m, 1H), 1.79-1.85 (m, 1H), 1.68-1.78 (m, 2H), 1.55-1.64 (m, 2H), 1.20-1.49 (m, 6H), 1.12 (s, 3H).

A solution of the oil and imidazole (182 mg, 2.65 mmol) in DMF (5 ml) was treated with triisopropylsilyl chloride (392 mg, 2.07 mmol). The resulting reaction mixture was stirred at room temperature for 20 hrs, then diluted with ethyl acetate, washed with water, dried over anhydrous $MgSO_4$, concentrated under reduced pressure. Column chromatography on silica gel afforded desired product 6 as a colorless oil, 307 mg (34% based on acrylate 4): $^1$H NMR ($CDCl_3$) δ 5.74 (s, 1H), 3.68 (t, J=6.0 Hz, 2H), 2.30-2.48 (m, 3H), 2.22-2.28 (m, 1H), 2.10 (ddd, J=13.2, 4.4, 3.6 Hz, 1H), 1.88-1.94 (m, 1H), 1.79-1.85 (m, 1H), 1.69-1.76 (m, 3H), 1.20-1.46 (m, 5H), 1.11 (s, 3H), 1.04-1.09 (m, 21H); $^{13}$C NMR ($CDCl_3$) δ 199.9, 171.6, 124.3, 63.6, 48.8, 39.6, 35.5, 34.2, 33.7, 31.9, 27.4, 26.7, 25.7, 18.2, 16.9, 12.2.

Example 4

2-(1,2,3,4,8,8α-hexahydro-8α-methylspiro[1',3'-dithiolane-2',6(7H)naphthalen]-1-yl)acetaldehyde (Structure 7)

A solution of potassium hexamethyldisalazide in toluene (0.5 M, 70 ml, 35 mmol) was added dropwise over 45 min to a solution of methoxymethyltriphenylphosphonium bromide (12 g, 35 mmol) in 80 ml of dry THF cooled to −30° C. under Ar atmosphere. The resulting mixture was allowed to warm up to 0° C. (ca. 1.5 hrs), then a solution of aldehyde 3 (4.68 g, 17.4 mmol) in 40 ml of dry THF was added dropwise over 30 min. The reaction mixture was allowed to warm to room temperature, then stirred at room temperature for 3 hrs. A mixture of 55 ml of 4N HCl and 55 ml of THF was added dropwise over 1.5 hrs, and the resulting mixture was vigorously stirred for 48 hrs. Water was then added to dissolve the precipitate, the layers were separated, and the aqueous layer was extracted with ether. Organic fractions were combined, washed with brine, dried over anhydrous $MgSO_4$, concentrated under reduced pressure to give brownish solid. The solid was treated with ether, and the white insoluble part was filtered off, washed with ether. Then the insoluble solid was treated with ether again, and the insoluble fraction was filtered off again. Ethereal filtrates were combined, and concentrated under reduced pressure to furnish light-brown solid, 14.30 g. Column chromatography on silica gel afforded the desired aldehyde 7, as a white solid, 3.84 g (78%): $^1$H NMR ($CDCl_3$) δ 9.73 (dd, J=3.2, 1.2 Hz, 1H), 5.55 (s, 1H), 3.68 (t, J=6.0 Hz, 2H), 3.34-3.38 (m, 3H), 3.20-3.25 (m, 1H), 2.52 (ddd, J=16.0, 2.0, 0.8 Hz, 1H), 2.10-2.19 (m, 4H), 2.03 (ddd, J=14.0, 2.0, 1.8 Hz, 1H), 1.73-1.86 (m, 3H), 1.50-1.61 (m, 2H), 1.55-1.65 (m, 2H), 1.33-1.39 (m, 2H), 0.98 (s, 3H); $^{13}$C NMR ($CDCl_3$) δ 202.8, 145.0, 125.6, 65.7, 45.2, 43.2, 40.3, 39.8, 38.0, 37.2, 36.9, 32.4, 28.9, 27.0, 18.4. Column chromatography of the mixed fraction afforded another 0.3 g (6%) of 7, total yield: 4.14 g (84%).

Example 5

4',4'a,5',6',7',8'-Hexahydro-4'a-methyl-8-(2-iodoethyl)-spiro[1,3-dithiolane-2,2'(3'H)-naphthalene (Structure 8)

Sodium borohydride (1.097 g, 29 mmol) was added slowly to a cooled to 0° C. solution of aldehyde 7 (4.12 g, 14.58 mmol) in 90 ml methanol and 35 ml THF. The reaction mixture was stirred at 0° C. for 1 hr and room temperature for 30 min. It was cooled again to 0° C., and saturated aq. $NH_4Cl$ (50 ml) was added cautiously. The precipitate was filtered off, and washed with ether. The filtrate was concentrated under reduced pressure to ca. 70 ml, then extracted with ethyl acetate. Organic extracts were combined, washed with saturated aq. $NH_4Cl$, and brine, dried over anhydrous $MgSO_4$, concentrated under reduced pressure to afford 4',4'a,5',6',7',8'-hexahydro-4'a-methyl-8-(2-hydroxyethyl)-spiro-1,3-dithiolane-2,2'(3'H)-naphthalne as a yellow oil, 4.28 g (>100%): $^1$H NMR ($CDCl_3$) δ 5.51 (s, 1H), 3.69-3.72 (m, 1H), 3.59-3.62 (m, 1H), 3.33-3.40 (m, 3H), 3.21-3.26 (m, 1H), 2.11-2.19 (m, 3H), 1.98-2.05 (m, 1H), 1.54-1.87 (m, 9H), 1.20-1.31 (m, 5H), 0.96 (s, 3H). Trituration with ether afforded 4.10 g (99%) of a white solid which was used in the following reaction.

Iodine (7.36 g, 29 mmol) was added over 20 min at 0° C. to a vigorously stirred solution of triphenylphosphine (7.61 g, 29 mmol) and imidazole (1.97 g, 29 mmol) in 75 ml of ether and 25 ml of acetonitrile. The resulting slurry was allowed to warm up to room temperature and stirred for 15 min. Then it was recooled to 0° C., and a solution of the alcohol (4.10 g, 14.4 mmol) in 40 ml of ether was added dropwise over 15 min. The resulting reaction mixture was stirred at room temperature for 3 hrs, then hexane (50 ml) was added resulting in the formation of precipitate. Most of the liquid was then decanted, and the remainder was cautiously treated with saturated aq. $NaHCO_3$ (50 ml). The mixture was extracted with hexanes, organic extracts were combined, washed with saturated aq. $NaHCO_3$, dried over anhydrous $MgSO_4$, concentrated under reduced pressure. Column chromatography on silica gel afforded the desired product 8 as a white solid, 4.90 g (85% over 2 steps): $^1$H NMR ($CDCl_3$) δ 5.52 (s, 1H), 3.29-3.38 (m, 4H), 3.22-3.27 (m, 1H), 3.05 (dt, J=8.4, 6.8 Hz, 1H), 1.98-2.18 (m, 5H), 1.76-1.82 (m, 2H), 1.45-1.68 (m, 3H), 1.19-1.30 (m, 3H), 0.95 (s, 3H); $^{13}$C NMR ($CDCl_3$) δ 145.7, 125.2, 65.9, 49.9, 40.3, 39.8, 38.0, 37.3, 36.8, 34.6, 32.6, 27.1, 27.0, 18.6, 6.1.

Example 6

4',4'a,5',6',7',8'-Hexahydro-4'a-methyl-8-{2-[4-(triisopropylsilyloxymethyl)phenyl]ethyl}-spiro-1,3-dithiolane-2,2'(3'H)-naphthalene (Structure 9)

A solution of tert-butyl lithium in pentane (1.7M, 44 ml, 70.94 mmol) was added dropwise over 30 min to a cooled to −78° C. solution of (p-bromobenzyloxy)triisopropylsilane (11.60 g, 33.78 mmol) in 30 ml of dry THF under an Ar atmosphere. The resulting yellow solution was stirred at −78° C. for 1.5 hrs, after which it was warmed up to dissolve all the precipitate (ca. 5 min). The solution was then recooled to −78° C. and added dropwise via cannula to a cooled to 0° C. suspension of copper (I) iodide (3.25 g, 16.89 mmol) in 20 ml of dry THF. The reaction mixture was stirred at 0° C. for 1 hr, then a solution of iodide 8 (3.33 g, 8.44 mmol) in 10 ml of dry THF was added in one portion. The reaction mixture was stirred at 0° C. for 1 hr, then at room temperature overnight. Then it was cooled to 0° C., and saturated aq. $NH_4Cl$ (50 ml) was added. The resulting mixture was stirred at room temperature for 30 min, then the precipitate was filtered off, the layers were separated, and the aqueous was extracted with ether. Organic fractions were combined, washed with saturated aq. $NH_4Cl$ and brine, dried over anhydrous $MgSO_4$, and concentrated under reduced pressure. Column chromatography on silica gel using 3:1 hexanes/toluene, then 25:1 hexanes/EtOAc as eluents furnished desired product 9 as a viscous colorless oil, 4.16 g (92%): $^1$H NMR ($CDCl_3$) δ 7.26 (d, J=8.0 Hz, 2H), 7.13 (d, J=8.0 Hz, 2H), 5.50 (s, 1H), 4.80 (s, 2H), 3.31-3.39 (m, 3H), 3.20-3.25 (m, 1H), 2.68-2.74 (m, 1H), 2.37-2.46 (m, 1H), 2.09-2.20 (m, 3H), 1.98-2.05 (m, 1H), 1.73-1.87 (m, 4H), 1.51-1.59 (m, 1H), 1.14-1.27 (m, 9H), 1.04-1.12 (m, 18H), 0.93 (s, 3H); $^{13}$C NMR ($CDCl_3$) δ 146.5, 141.6, 139.2, 128.3, 1216.0, 124.8, 66.1, 65.1, 49.1, 40.2, 39.7, 38.2, 37.6, 37.1, 34.7, 32.9, 32.3, 27.6, 27.4, 18.2, 12.3.

Example 7

4α-Methyl-5-{2-[4-(triisopropylsilyloxymethyl)phenyl]ethyl}-4,4α,5,6,7,8-hexahydro-3H-naphthalen-2-one (Structure 10)

A solution of mercury (II) perchlorate hydrate (13.55 g, 32.45 mmol) in 25 ml of methanol was added dropwise over 10 min to a stirred solution of 9 (3.60 g, 7.9 mmol) and 2,6-di-tert-butyl-4-methylpyridine (6.66 g, 32.45 mmol) in 50 ml of chloroform. The resulting yellow reaction mixture was stirred at room temperature for 30 min, then the precipitate was filtered off. The filtrate was treated with saturated aq. NaHCO$_3$, and filtered again to remove white voluminous precipitate. The clear filtrate was extracted with chloroform. Organic fractions were combined, washed with brine, dried over anhydrous MgSO$_4$, concentrated under reduced pressure. Column chromatography on silica gel afforded desired product 10 as a colorless oil, 1.64 g (46%): $^1$H NMR (CDCl$_3$) δ 7.27 (d, J=8.0 Hz, 2H), 7.13 (d, J=8.0 Hz, 2H), 5.72 (s, 1H), 4.81 (s, 2H), 2.78 (ddd, J=14.2, 10.2, 4.8 Hz, 1H), 2.21-2.49 (m, 5H), 2.02-2.08 (m, 1H), 1.88-1.95 (m, 2H), 1.77-1.85 (m, 1H), 1.61 (dt, J=14.2, 5.2 Hz, 1H), 1.16-1.43 (m, 9H), 1.02-1.14 (m, 20H); $^{13}$C NMR (CDCl$_3$) δ 199.8, 171.3, 140.9, 139.5, 128.3, 126.1, 124.4, 65.1, 48.2, 39.4, 35.2, 34.3, 34.1, 33.7, 31.7, 27.2, 26.6, 28.3, 17.0, 12.3.

Example 8

3-(4α-Methyl-4,4α,5,6,7,8-hexahydro-1H-benzo[f]indazol-5-yl)propan-1-ol (Structure 12)

A solution of lithium diisopropylamide (2.0M, 65 μl, 0.13 mmol) was added to a solution of ketone 6 (20 mg, 0.067 mmol) in 1 ml of dry ether cooled to −78° C. under an Ar atmosphere. The reaction solution was stirred at −78° C. for 45 min, then 2,2,2-trifluoroethyl formate (90 mg, 0.75 mmol) was added in one portion. The reaction mixture was stirred at −78° C. for 2 hrs, then quickly warmed up to room temperature in a water bath and allowed to sit at room temperature for 15 min. Saturated aq. NH$_4$Cl was added, the layers were separated, and the aqueous was extracted with ether. Organic fractions were combined, washed with saturated aq. NH$_4$Cl, dried over anhydrous MgSO$_4$, and concentrated under reduced pressure to afford crude β-ketoaldehyde 11 as an orange oil, 23 mg.

The oil was then dissolved in 1 ml of ethanol and treated with hydrazine hydrate (17 mg, 33 mmol). The resulting mixture was stirred at room temperature for 24 hrs, then water was added, and the resulting mixture was extracted with ether. Ethereal extracts were combined, washed with brine, dried over anhydrous MgSO$_4$, and concentrated under reduced pressure to furnish 4α-methyl-5-(3-triisopropylsilyloxypropyl)-4,4α,5,6,7,8-hexahydro-1H-benzo[f]indazole as an orange oil, 16 mg.

The oil was dissolved in 0.5 ml of dry THF and treated with a solution of tetrabutylammonium fluoride in THF (1.0 M, 0.2 ml, 0.2 mmol). The reaction mixture was stirred at room temperature for 30 min, then was quenched with saturated aq. NH$_4$Cl. The mixture was extracted with ether; ethereal extracts were combined, washed with saturated aq. NH$_4$Cl and brine, dried over anhydrous MgSO$_4$, and concentrated under reduced pressure. Column chromatography on silica gel afforded desired product 12 as a light-yellow oil, 7 mg (41% based on 6): $^1$H NMR (CDCl$_3$) δ 7.22 (s, 1H), 6.19 (s, 1H), 3.68 (t, J=7.2 Hz, 2H), 2.91 (d, J=15.6 Hz, 1H), 2.44 (d, J=15.2 Hz, 1H), 2.34-2.37 (m, 2H), 1.67-1.85 (m, 3H), 1.50-1.67 (m, 2H), 1.19-1.48 (m, 5H), 1.05-1.19 (m, 1H), 0.90 (s, 3H).

Example 9

3-(4α-Methyl-4,4α,5,6,7,8-hexahydronaphtho[2,3-d]isoxazol-5-yl)propan-1-ol (Structure 13)

A mixture of 11 (synthesized as described above, 43 mg, 0.108 mmol), hydroxylamine hydrochloride (17 mg, 0.25 mmol), and sodium acetate (21 mg, 0.25 mmol) in glacial acetic acid (1 ml) was stirred at room temperature for 24 hrs. Then the reaction mixture was slowly added to an ice/saturated aq. NaHCO$_3$ mixture. The resulting mixture was extracted with ethyl acetate. Organic fractions were combined, washed with saturated aq. NaHCO$_3$, dried over anhydrous MgSO$_4$, and concentrated under reduced pressure. Column chromatography on silica gel afforded 4α-methyl-5-(3-triisopropylsilyloxypropyl)-4,4α,5,6,7,8-hexahydronaphtho[2,3-d]isoxazole as a yellow oil, 7 mg (16%): $^1$H NMR (CDCl$_3$) δ 7.98 (s, 1H), 6.17 (d, J=1.2 Hz, 1H), 3.70 (t, J=6.4 Hz, 2H), 2.80 (d, J=15.6 Hz, 1H), 2.50 (d, J=15.6 Hz, 1H), 2.35-2.45 (m, 2H), 1.80-1.88 (m, 2H), 1.70-1.79 (m, 1H), 1.52-1.63 (m, 2H), 1.36-1.49 (m, 3H), 1.21-1.29 (m, 2H), 1.04-1.16 (m, 25H), 0.94 (s, 3H).

A solution of 4α-methyl-5-(3-triisopropylsilyloxypropyl)-4,4α,5,6,7,8-hexahydronaphtho[2,3-d]isoxazole (7 mg, 0.017 mmol), and trifluoroacetic acid (20 mg,) in 0.3 ml of THF and 0.1 ml of water was stirred at room temperature for 8 hrs. Then it was diluted with saturated aq. NaHCO$_3$ and extracted with ether. Ethereal extracts were combined, washed with brine, dried over anhydrous MgSO$_4$, and concentrated under reduced pressure. Column chromatography on silica gel afforded the desired product 13 as a light-yellow oil, 2.5 mg (71%): $^1$H NMR (CDCl$_3$) δ 7.99 (s, 1H), 6.18 (d, J=1.2 Hz, 1H), 3.68 (t, J=6.4 Hz, 2H), 2.82 (d, J=16.0 Hz, 1H), 2.50 (d, J=15.6 Hz, 1H), 2.35-2.42 (m, 2H), 1.81-1.90 (m, 2H), 1.71-1.79 (m, 1H), 1.52-1.63 (m, 2H), 1.35-1.52 (m, 3H), 1.24-1.31 (m, 2H), 1.09-1.20 (m, 1H), 0.95 (s, 3H).

Example 10

3-(2,4α-Dimethyl-4,4α,5,6,7,8-hexahydro-2H-benzo[f]indazol-5-yl)-propan-1-ol (Structure 14)

Compound 14 was synthesized following the procedure for the synthesis of 12, but employing 76 mg (0.2 mmol) of 11 and methylhydrazine (18 mg, 0.4 mmol). A 2:1 mixture of isomers was obtained. Column chromatography on silica gel afforded 14 (a major isomer) as a colorless oil, 11 mg (21% based on 6): $^1$H NMR (CDCl$_3$) δ 6.97 (s, 1H), 6.16 (s, 1H), 3.80 (s, 3H), 3.67 (t, J=6.4 Hz, 2H), 2.86 (d, J=15.2 Hz, 1H), 2.42 (d, J=15.6 Hz, 1H), 2.33-2.38 (m, 2H), 1.70-1.83 (m, 3H), 1.56-1.68 (m, 2H), 1.35-1.52 (m, 3H), 1.20-1.30 (m, 2H), 1.09-1.20 (m, 1H), 0.90 (s, 3H).

Column chromatography of the mixed fractions (7 mg, 13%) on silica gel afforded minor isomer 3-(1,4α-dimethyl-4,4α,5,6,7,8-hexahydro-2H-benzo[f]indazol-5-yl)-propan-1-ol (15) as a colorless oil, 2 mg: $^1$H NMR (CDCl$_3$) δ 7.17 (s, 1H), 6.01 (d, J=1.6 Hz, 1H), 3.76 (s, 3H), 3.68 (t, J=6.4 Hz, 2H), 2.86 (d, J=15.6 Hz, 1H), 2.43 (d, J=15.6 Hz, 1H), 2.33-2.38 (m, 2H), 1.71-1.86 (m, 3H), 1.56-1.68 (m, 2H), 1.35-1.52 (m, 3H), 1.20-1.30 (m, 2H), 1.05-1.14 (m, 1H), 0.89 (s, 3H).

Example 11

3-(1-[4-Fluorophenyl]-4α-Methyl-4,4α,5,6,7,8-hexahydro-1H-benzo[f]indazol-5-yl)propan-1-ol (Structure 16)

1-(4-Fluorophenyl)-4α-methyl-5-(3-triisopropylsilyloxy)-4,4α,5,6,7,8-hexahydro-1H-benzo[f]indazole was synthesized following the procedure described for 13, but employing 4-fluorophenylhydrazine hydrochloride, and the deprotection was done using nBu$_4$NF as described for 12: $^1$H NMR (CDCl$_3$) δ 7.44-7.47 (m, 2H), 7.39 (s, 1H), 7.15 (t, J=8.2 Hz, 2H), 6.11 (d, J=2.4 Hz, 1H), 3.68 (dt, J=6.4, 1.6 Hz, 2H), 2.94 (d, J=15.6 Hz, 1H), 2.52 (d, J=15.2 Hz, 1H), 2.26-2.42 (m, 2H), 1.70-1.88 (m, 2H), 1.58-1.69 (m, 2H), 1.24-1.54 (m, 5H), 1.08-1.21 (m, 1H), 0.90 (s, 3H); $^{13}$C NMR (CDCl$_3$) δ 161.6 (J$_{CF}$=245.5 Hz), 150.6, 138.1, 137.1, 136.2, 125.5 (J$_{CF}$=8.7 Hz), 116.2 (J$_{CF}$=22.8 Hz), 114.4, 109.4, 63.4, 49.5, 41.2, 34.3, 33.4, 31.8, 28.1, 26.6, 26.3, 17.9.

Example 12

3-(4α-Methyl-1-(2,2,2-Trifluoroethyl)-4,4α,5,6,7,8-hexahydro-1H-benzo[f]indazol-5-yl)propan-1-ol (Structure 17)

Compound 17 was synthesized as described for 12 utilizing 2,2,2,-trifluoroethylhydrazine (70% solution in water): $^1$H NMR (CDCl$_3$) δ 7.29 (s, 1H), 5.99 (s, 1H), 4.52-4.68 (m, 2H), 3.68 (dt, J=6.4, 1.6 Hz, 2H), 2.87 (d, J=15.6 Hz, 1H), 2.46 (d, J=15.2 Hz, 1H), 2.28-2.42 (m, 2H), 1.70-1.88 (m, 3H), 1.31-1.66 (m, 5H), 1.22-1.29 (m, 2H), 1.11-1.18 (m, 1H), 0.90 (s, 3H).

Example 13

{4-[2-(4a-Methyl-4,4a,5,6,7,8-hexahydro-1H-benzo[f]indazol-5-yl)-ethyl]-phenyl}-methanol (Structure 18)

Compound 18 was synthesized following the procedure for 12, but utilizing ketone 10 (112 mg, 0.25 mmol), hydrazine hydrate (31 mg, 0.62 mmol). White solid (recrystallized from CHCl$_3$), $^1$H NMR (CDCl$_3$) δ 7.30 (d, J=7.6 Hz, 2H), 7.16-7.21 (m, 3H), 6.16 (s, 1H), 4.66 (s, 2H), 2.85 (d, J=15.6 Hz, 0.75H), 2.78-2.86 (m, 1H), 2.67 (d, J=15.2 Hz, 1H), 2.45-2.60 (m, 1H), 2.31-2.38 (m, 2H), 2.04 (d, J=15.6 Hz, 0.25H), 1.94 (d, J=13.2 Hz, 1H), 1.78-1.90 (m, 2H), 1.55-1.60 (m, 0.5H), 1.26-1.43 (m, 4H), 0.89 (s, 3H).

Example 14

{4-[2-(4a-Methyl-4,4a,5,6,7,8-hexahydro-naphtho[2,3-d]isoxazol-5-yl)-ethyl]-phenyl}-methanol (Structure 19)

Compound 19 was synthesized following the procedure for 13 but employing ketone 10 (112 mg, 0.25 mmol). Colorless oil: $^1$H NMR (CDCl$_3$) δ 7.97 (s, 1H), 7.30 (d, J=8.4 Hz, 2H), 7.18 (d, J=8.0 Hz, 2H), 6.16 (d, J=1.2 Hz, 1H), 4.67 (s, 2H), 2.79-2.86 (m, 1H), 2.75 (d, J=16.0 Hz, 1H), 2.32-2.53 (m, 4H), 1.76-1.98 (m, 4H), 1.24-1.49 (m, 4H), 0.94 (s, 3H).

Example 15

{4-[2-(4a-Methyl-1-(4-fluorophenyl)-(4,4a,5,6,7,8-hexahydro-1H-benzo[f]indazol-5-yl)-ethyl]-phenyl}-methanol (Structure 20)

1-(4-Fluorophenyl)-4α-methyl-5-(2-[4-{triisopropylsilyloxymethyl}phenyl]ethyl)-4,4α,5,6,7,8-hexahydro-1H-benzo[f]indazole was synthesized following the procedure for the synthesis of 13 but employing ketone 10 (112 mg, 0.25 mmol) and 4-fluorophenylhydrazine hydrochloride (49 mg, 0.3 mmol).

Deprotection was achieved using nBu$_4$NF as described for 12. Off-white solid, 39 mg (39% based on 10): $^1$H NMR (CDCl$_3$) δ 7.40-7.45 (m, 2H), 7.35 (s, 1H), 7.29 (d, J=8.0 Hz, 2H), 7.19 (d, J=7.6 Hz, 2H), 7.13 (t, J=8.6 Hz, 2H), 6.08 (d, J=1.6 Hz, 1H), 4.65 (s, 2H), 2.87 (d, J=15.6 Hz, 1H), 2.78-2.86 (m, 1H), 2.24-2.56 (m, 4H), 2.04 (br s, 1H), 1.81-1.98 (m, 2H), 1.30-1.45 (m, 4H), 0.94 (s, 3H).

Example 16

4α-Methyl-3-trifluoroacetyl-5-[3-(triisopropylsiloxy)propyl]-4,4α,5,6,7,8-hexahydro-3H-naphthalen-2-one (Structure 21)

Diisopropylamine (freshly distilled from CaH$_2$, 86 μl, 0.61 mmol) was added to a solution of n-butyl lithium in hexanes (2.41 M, 253 μl, 0.61 mmol) cooled to −40° C. under Ar atmosphere. The reaction mixture was stirred at −40° C. for 15 min, then cooled to −78° C. A solution of ketone 6 (155 mg, 0.41 mmol) in 1 ml of dry ether was added dropwise. The resulting mixture was stirred at −78° C. for 45 min, then 2,2,2-trifluoroethyl trifluoroacetate (482 mg, 2.46 mmol) was added in one portion. The reaction mixture was stirred at −78° C. for 2 hrs, then was quickly warmed up to room temperature in a water bath and allowed to sit at room temperature for 15 min. Saturated aq. NH$_4$Cl was added, the layers were separated, and the aqueous layer was extracted with ether. Organic fractions were combined, washed with saturated aq. NH$_4$Cl, dried over anhydrous MgSO$_4$, and concentrated under reduced pressure Column chromatography on silica gel afforded desired product 21 as a dark-brown oil, 50 mg (26%): $^1$H NMR (CDCl$_3$) δ 5.89 (s, 1H), 3.70 (m, 2H), 2.90 (dd, J=15.2, 1.6 Hz, 1H), 2.38-2.42 (m, 2H), 2.29 (d, J=15.2 Hz, 1H), 1.81-1.97 (m, 2H), 1.58-1.75 (m, 3H), 1.18-1.34 (m, 5H), 1.00-1.16 (m, 24H), 0.98 (s, 3H); $^{13}$C NMR (CDCl$_3$) δ 187.2, 173.5, 167.0 (J$_{CF}$=34.2 Hz), 121.4, 118.9 (J$_{CF}$=280.6 Hz), 103.0, 63.5, 48.2, 40.7, 34.5, 33.5, 31.9, 27.2, 26.4, 25.9, 18.2, 17.6, 12.2.

Example 17

3-(4α-Methyl-1-3-trifluoromethyl-4,4α,5,6,7,8-hexahydro-1H-benzo[f]indazol-5-yl)propan-1-ol (Structure 22)

Structure 22 was synthesized following the procedure described for 12, employing 21 (29 mg, 0.061 mmol) and hydrazine hydrate (17 mg, 0.34 mmol). Yellow oil, 7 mg (37%): $^1$H NMR (CDCl$_3$) δ 6.04 (s, 1H), 5.81 (br s, 1H), 3.65 (t, J=6.2 Hz, 2H), 3.15 (dd, J=13.6, 4.8 Hz, 1H), 2.26-2.34 (m, 2H), 2.06 (dd, J=12.8, 5.2 Hz, 1H), 1.70-1.88 (m, 3H), 1.31-1.66 (m, 5H), 1.22-1.29 (m, 2H), 1.11-1.18 (m, 1H), 0.90 (s, 3H).

Example 18

3-(4a-Methyl-3-trifluoromethyl-4,4a,5,6,7,8-hexahydro-naphtho[2,3-d]isoxazol-5-yl)-propan-1-ol (Structure 23)

Structure 23 was synthesized following the procedure described for 13, employing 21 (26 mg, 0.055 mmol), hydroxylamine hydrochloride (19 mg, 0.275 mmol), and sodium acetate (23 mg, 0.275 mmol). Light-yellow oil, 8 mg (47%): $^1$H NMR (CDCl$_3$) δ 6.11 (s, 1H), 3.67 (t, J=6.4 Hz, 2H), 3.43 (dd, J=14.2, 5.0 Hz, 1H), 2.32-2.34 (m, 2H), 2.09 (dd, J=12.8, 5.2 Hz, 1H), 1.79-1.90 (m, 2H), 1.56-1.76 (m, 4H), 1.39-1.49 (m, 1H), 1.18-1.36 (m, 3H), 1.09-1.20 (overlapping m, 1H+s, 3H).

Example 19

Activity of Synthesized Ligands

Binding affinity of the synthesized ligands was evaluated by competition fluorescence polarization assay using recombinant rat AR LBD, and the results summarized in Table 1. All ligands with a bulky right-hand extension, such as compounds 18-20 in FIG. 5, performed poorly in this assay, with even the best compounds binding AR only weakly. Structures with a smaller group attached to the right-hand side of the structure, exemplified by compounds 14-17 and 22-23 in FIG. 5, had considerably improved binding affinity, and afforded potent AR ligands. In Table 1, RBA stands for relative binding affinity, and is defined as the ratio of $K_d$ of the test compound to $K_d$ of DHT multiplied by 100.

TABLE 1

| Compound | RBA (DHT = 100) |
|---|---|
| 18 | <0.1 |
| 19 | <0.1 |
| 20 | 0.12 |
| 24† | 0.12 |
| 12 | 1 |
| 16 | 19 |

†Mixture of isomers.

Example 20

Transactivation Assay

Transactivation assays were performed in U2OS cells transiently transfected with an AR expression vector and a reporter expression vector containing luciferase gene downstream of mouse mammary tumor viral long terminal repeat (MMTV-LTR) promoter. The experimental procedures included the following. U2OS cells were grown in DME H-21 media supplemented with 100 mg/L streptomycin sulfate, 100 units/ml of penicillin G and 10% fetal bovine serum (FBS). Cells were plated into tissue culture treated 96-well plates (30,000 cells/well) and incubated at 37° C. for 24 hrs. Cells were then transfected using the Lipofectamine PLUS reagent (Invitrogen). DNA-lipid complexes of AR (20 ng/well), murine mammary tumor virus LTR-luciferase (MMTV-luc, 100 ng/well), Renilla luciferase (10 ng/well), the PLUS reagent (1 µl/well) and Lipofectamine (0.67 µl/well) in serum free DME H-21 media without phenol red were prepared according to manufacturer's specifications. Complexes (50 µl/well) were added to cells and incubated for 3 hrs at 37° C. Complexes were removed and solutions of DHT ($10^{-7}$-$10^{-13}$ M) or test compounds (0.1-10 mM) with DHT (0.1 nM) in hormone-stripped media (the same as the growth media, but supplemented with 10% charcoal-stripped FBS and without phenol red) were added. The cells were incubated at 37° C. for 24 hrs, then media was removed and the cells were washed with 100 ml of $Ca^{2+}$, $Mg^{2+}$-free phosphate buffered saline (PBS). Lysis was achieved by adding 50 ml of Passive Lysis Buffer (Promega Corp.) and shaking the plate for 15 min. The Dual-Luciferase Reporter Assay system (Promega Corp.) was used to assay luciferase activity following the manufacturer's protocol. Luminescence was measured for 0.1 s/well on an Analyst HT Detection System (LJL Biosystems).

Figure 7:
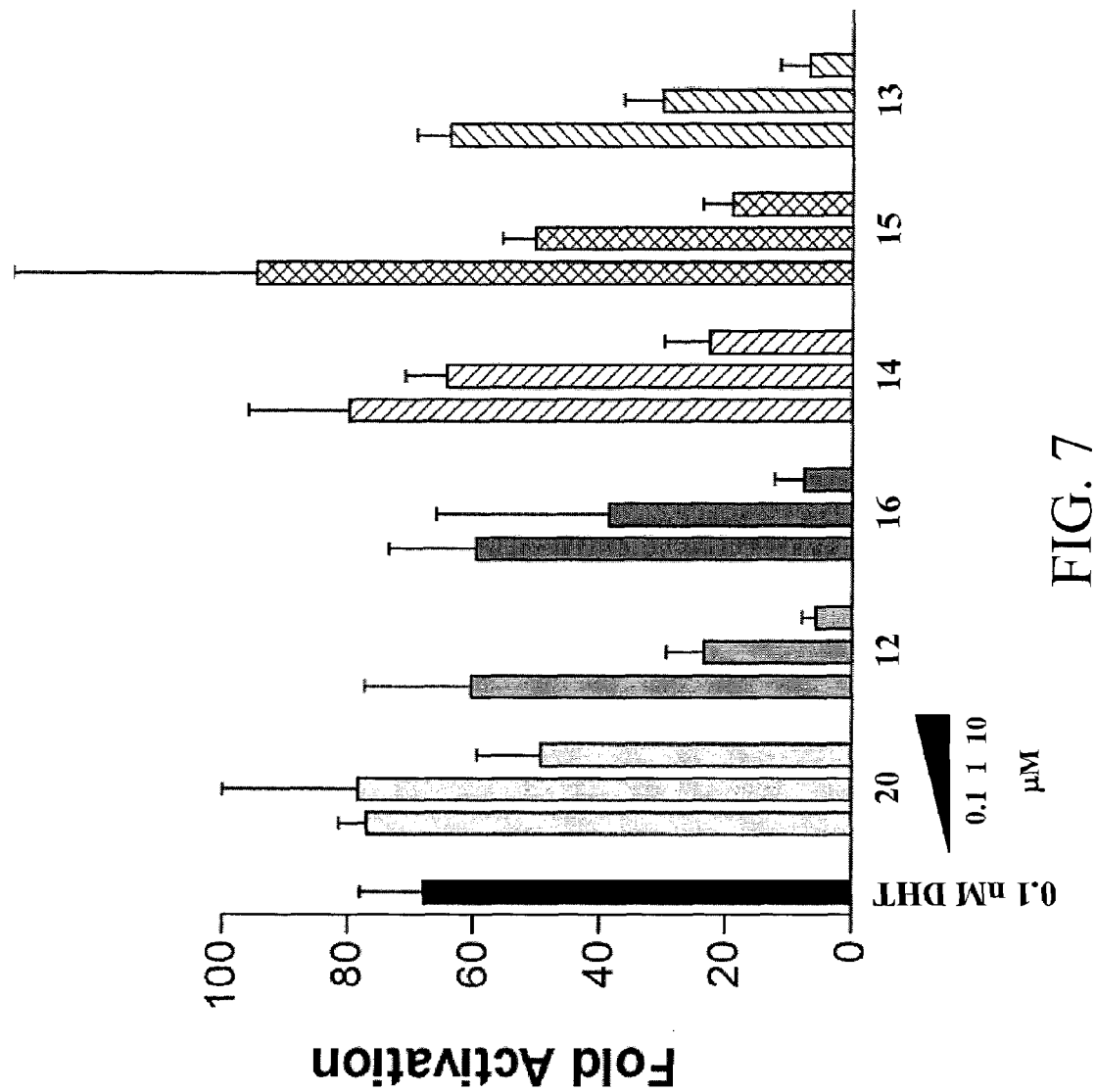
FIG. 7 depicts repression of AR transcriptional activity.

The strongest binding compound of those that have a bulky substituent on the right hand side (compound 20), and five compounds of those that have a smaller substituent (compounds 14-16, 12 and 13) were evaluated in these assays. None of the tested compounds exhibited any agonist activity, failing to activate gene transcription above the background level even at the 10 µM concentration. However, all compounds caused repression of transcription when tested against an $EC_{50}$ concentration of DHT (FIG. 7). It is noteworthy that there is no direct correlation between the binding affinity and $IC_{50}$ of these compounds. The bulky right-hand side extension appears to significantly reduce the antagonist potency. Out of the heterocycles tested, an unsubstituted pyrazole, isoxazole, and 4-flurophenylpyrazole prove to be the most potent, inhibiting transcription almost to the background level at the 10 µM concentration ($IC_{50}$<1-3 µM).

Example 21

LNCaP Cell Proliferation Assay

LNCaP cells were grown in RPMI-1640 media adjusted to contain 4.5 g/L glucose, 10 mM HEPES, 1 mM sodium pyruvate, and supplemented with 100 mg/L streptomycin sulfate, 100 units/ml of penicillin G and 10% fetal bovine serum. For the assay, cells were grown in the hormone-depleted media (the same media as the growth media, but supplemented with 10% charcoal-stripped FBS and without phenol red) for 3 days, then plated in tissue culture treated 96-well plates (10,000 cell/well) and incubated at 37° C. for 24 hrs. Media was removed; solutions of test compounds in hormone-stripped media (0.1-10 mM) with or without DHT (1 nM) were added (100 µl/well). Cells were incubated at 37° C. for 7 days, and media was changed on the 3rd and 6th days. At the end of the incubation period, the number of cells was determined using CellTiter-Glo Luminescent Cell Viability assay (Promega Corp.) following the manufacturer's protocol. Luminescence was measured for 0.1 s/well on an Analyst HT Detection System (LJL Biosystems).

Figure 8A:
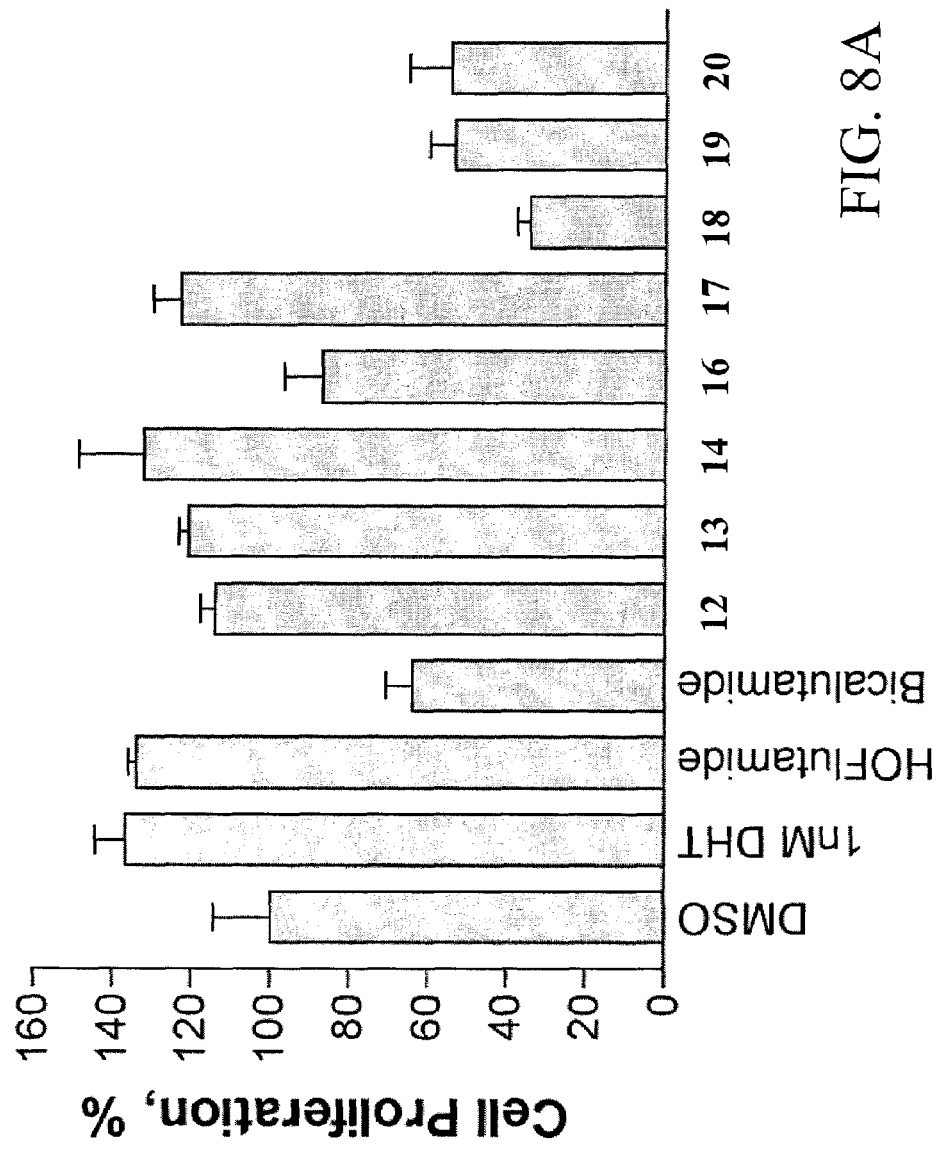
FIGS. 8A, 8B, and 8C show experimental data for LNCaP proliferation with various compounds of the present invention.
Figure 8B:
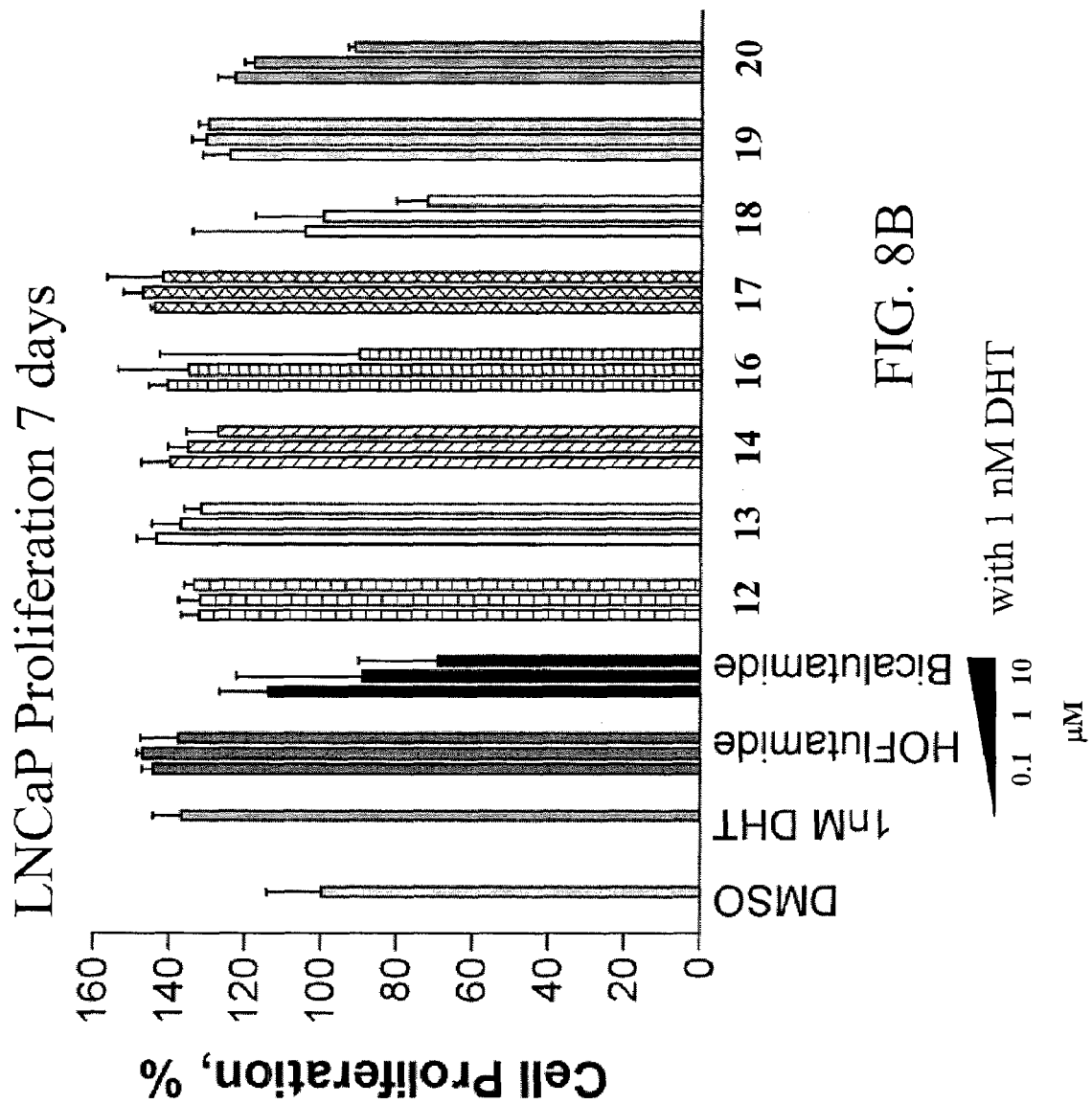
Figure 8C:
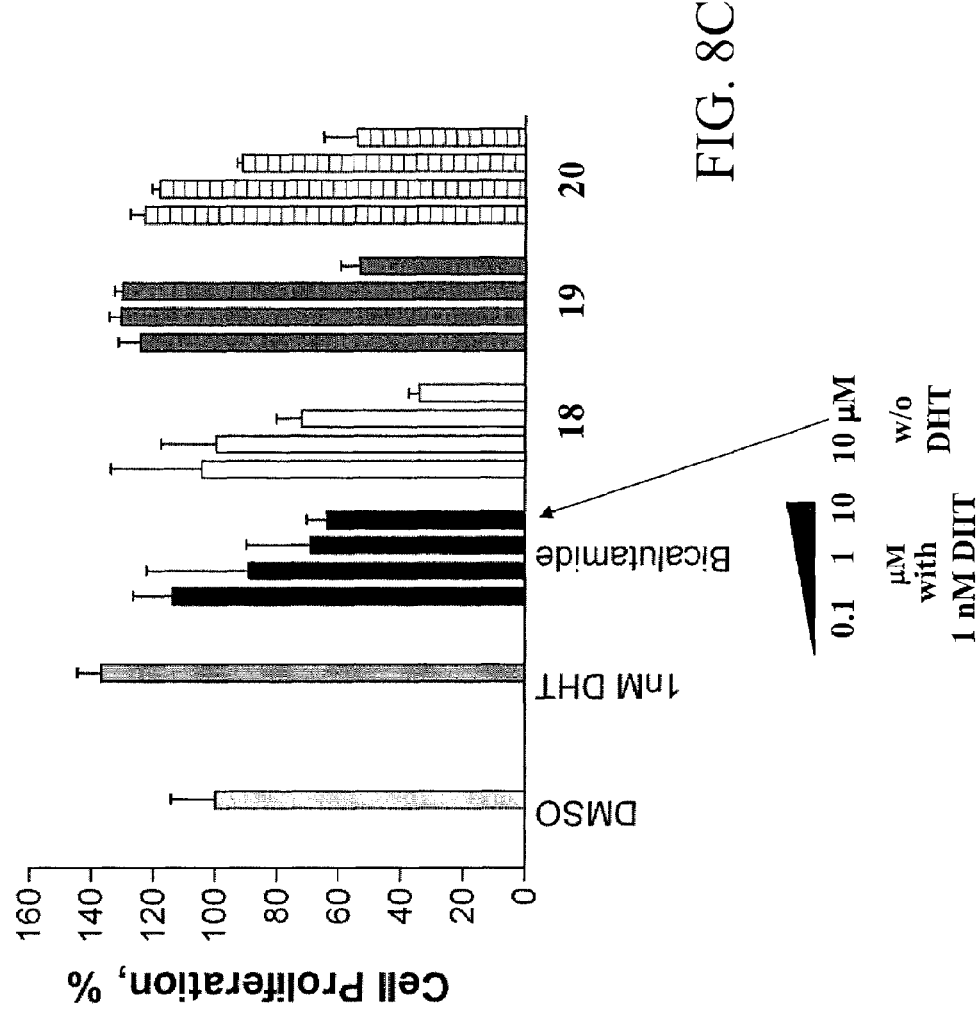

Results for compounds 18, 19, 20, 12, 16, 14, 17, and 13, are shown in FIGS. 8A-8C.

A number of embodiments of the invention have been described. Nevertheless, it will be understood that various modifications may be made without departing from the spirit and scope of the invention. Accordingly, the present embodiments are to be considered as illustrative and not restrictive, and the invention is not to be limited to the details given herein, but may be modified within the scope and equivalents of the appended claims.

All patents and other publications cited herein are incorporated herein by reference in their entirety for all purposes.

What is claimed is:

1. A compound according to structural formula Ib,

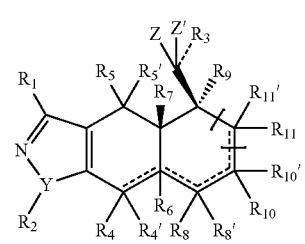

or a pharmaceutically available salt thereof wherein:

Y is nitrogen or oxygen, and when Y is oxygen, $R_2$ is absent;

Z is hydrogen, or is absent;

Z' is hydrogen, or is absent;

n is 1;

$R_1$ is hydrogen, alkyl, substituted alkyl, perfluoro alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, nitro, halo, thio, hydroxyl, heteroalkyl, or substituted heteroalkyl;

$R_2$ is hydrogen, alkyl, substituted alkyl, perfluoro alkyl, acyl, substituted acyl, alkoxycarbonyl, substituted alkoxycarbonyl, aryl, arylalkyl, substituted arylalkyl, aryloxycarbonyl, substituted aryloxycarbonyl, carbamoyl, substituted carbamoyl, carboxy, cyano, heteroalkyl, or substituted heteroalkyl;

$R_3$ is —(CRR')$_m$W, —CR=CR'W, =CRW, or —C≡CW, wherein m=1-10;

R and R' is each independently hydrogen, cyano, nitro, halo, thio, carboxy, alkyl, substituted alkyl, aryl, substituted aryl, arylalkyl, or substituted arylalkyl; and wherein W is alkyl, substituted alkyl, aryl, substituted aryl, carbamoyl, substituted carbamoyl, carboxy, cyano, heteroalkyl, substituted heteroalkyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, nitro, halo, thio, or hydroxyl;

each of $R_4$, $R_8$, $R_{10}$, and $R_{11}$ is hydrogen;

each of $R_4'$, $R_8'$, $R_{10}'$, and $R_{11}'$ is hydrogen or when attached to a ring carbon atom that itself is bonded to an adjacent ring carbon atom by a double bond, is absent;

$R_5$ and $R_5'$ are hydrogen;

$R_6$ is hydrogen, or when attached to a ring carbon atom that itself is bonded to an adjacent ring carbon atom by a double bond, is absent;

$R_7$ is hydrogen, alkyl, substituted alkyl, acyl, substituted acyl, acylamino, substituted acylamino, alkoxy, substituted alkoxy, amino, alkylamino, substituted alkylamino, dialkylamino, substituted dialkylamino, alkylsulfonyl, substituted alkylsulfonyl, alkylsulfinyl, substituted alkylsulfinyl, alkylthio, substituted alkylthio, alkoxycarbonyl, substituted alkoxycarbonyl, aryl, substituted aryl, arylalkyl, substituted arylalkyl, aryloxycarbonyl, substituted aryloxycarbonyl, carbamoyl, substituted carbamoyl, carboxy, cyano, halo, nitro, thio, hydroxyl, heteroalkyl, substituted heteroalkyl;

$R_9$ is hydrogen;

the bond in formulae Ia and Ib that is shown with a dashed line is a single, double, or triple bond, and when it is a double or a triple bond, one or more of Z and Z' is absent, such that the carbon atom to which Z, Z', and $R_3$ is attached has a normal valence; and one or more of the bonds in formulae Ia and Ib that are shown with single and dashed lines is a double bond and one or more of $R_4'$, $R_8'$, $R_{10}'$, and $R_{11}'$ is absent, such that normal valences of carbon atoms in the rings are satisfied.

2. The compound of claim 1 wherein $R_1$ and $R_2$ are independently hydrogen, or alkyl.

3. The compound of claim 1, wherein $R_1$ is selected from the group consisting of: hydrogen, and $CF_3$.

4. The compound of claim 1, wherein Y is nitrogen, and $R_2$ is selected from the group consisting of: hydrogen, methyl, and —$CH_2CF_3$.

5. The compound of claim 1, wherein $R_4'$ and $R_6$ are absent and there is a double bond between the two ring carbon atoms to which they are respectively attached.

6. The compound of claim 5 wherein all other bonds marked with solid and dashed lines are single bonds.

7. The compound of claim 1, wherein $R_6$ and $R_8'$ are absent and there is a double bond between the two ring carbon atoms to which they are respectively attached.

8. The compound of claim 1, wherein $R_7$ is methyl.

9. The compound of claim 1, wherein $R_9$ is hydrogen.

10. The compound of claim 1, wherein Z and Z' are both hydrogen.

11. The compound of claim 1, wherein $R_3$ is $(CH_2)_m$W, wherein m=1-6, and W=OH, para-$C_6H_4CH_2OH$, CH=CHCH$_2$CH$_3$, CH(CH$_3$)OH, C(CH$_3$)$_2$OH, CH(Ph)OH, OCH$_3$, NH$_2$, NHAc, or 2-pyrimidinyl.

12. The compound of claim 11, wherein m=1.

13. The compound of claim 11 wherein $R_3$ is C≡CW, and W=hydroxyalkyl.

14. The compound of claim 11, wherein W=CH$_2$OH.

15. The compound of claim 1, wherein Z is hydrogen and Z' is absent.

16. The compound of claim 15, wherein $R_3$ is =CRW, and wherein W is alkyl or substituted alkyl.

17. The compound of claim 16, wherein W is CH$_2$OH.

18. The compound of claim 16, wherein $R_3$ is —CR=CR'W, wherein W=hydroxyalkyl.

19. The compound of claim 1, wherein Y is nitrogen.

20. A composition comprising the compound of claim 1.

21. A method for selectively modulating the activation, repression, agonism and antagonism effects of the androgen receptor in a patient, comprising administering to said patient a therapeutically effective amount of a composition according to claim 20.

22. A method for selectively modulating the activation, repression, agonism and antagonism effects of the androgen receptor in a patient, comprising administering to said patient a therapeutically effective amount of a compound according to claim 1.

* * * * *